(12) United States Patent
Kitahara et al.

(10) Patent No.: US 11,939,695 B2
(45) Date of Patent: Mar. 26, 2024

(54) QUARTZ GLASS CRUCIBLE, MANUFACTURING METHOD OF SILICON SINGLE CRYSTAL USING THE SAME, AND INFRARED TRANSMISSIVITY MEASUREMENT METHOD AND MANUFACTURING METHOD OF QUARTZ GLASS CRUCIBLE

(71) Applicant: SUMCO CORPORATION, Tokyo (JP)

(72) Inventors: Ken Kitahara, Akita (JP); Masanori Fukui, Akita (JP); Hiroshi Kishi, Akita (JP); Tomokazu Katano, Tokyo (JP); Eriko Kitahara, Akita (JP)

(73) Assignee: SUMCO CORPORATION, Tokyo (JP)

( * ) Notice: Subject to any disclaimer, the term of this patent is extended or adjusted under 35 U.S.C. 154(b) by 145 days.

(21) Appl. No.: 17/413,929

(22) PCT Filed: Dec. 16, 2019

(86) PCT No.: PCT/JP2019/049120
§ 371 (c)(1),
(2) Date: Jun. 14, 2021

(87) PCT Pub. No.: WO2020/137648
PCT Pub. Date: Jul. 2, 2020

(65) Prior Publication Data
US 2022/0090291 A1    Mar. 24, 2022

(30) Foreign Application Priority Data

Dec. 27, 2018  (JP) ................................ 2018-244361
Dec. 27, 2018  (JP) ................................ 2018-244362

(51) Int. Cl.
*C30B 15/10*    (2006.01)
*C03B 20/00*    (2006.01)
(Continued)

(52) U.S. Cl.
CPC .............. *C30B 15/10* (2013.01); *C03B 20/00* (2013.01); *C03C 19/00* (2013.01); *C30B 29/06* (2013.01);
(Continued)

(58) Field of Classification Search
CPC ..... C03B 19/095; C03B 20/00; C03C 17/004; C03C 17/005; C03C 17/245; C03C 17/25;
(Continued)

(56) References Cited

U.S. PATENT DOCUMENTS

2010/0107970 A1    5/2010  Kodama et al.
2010/0236473 A1*   9/2010  Kishi .................... C03C 3/06
                                                    65/33.9
2022/0090290 A1    3/2022  Fujita et al.

FOREIGN PATENT DOCUMENTS

CN    106868583 A      6/2017
EP        1024118 A2 * 8/2000 ........... C03B 19/095
(Continued)

OTHER PUBLICATIONS

International Search Report (ISR) dated Feb. 18, 2020, issued for International application No. PCT/JP2019/049120. (2 pages).
(Continued)

*Primary Examiner* — Hua Qi
(74) *Attorney, Agent, or Firm* — Law Office of Katsuhiro Arai

(57) ABSTRACT

A quartz glass crucible 1 having a cylindrical side wall portion 10a, a bottom portion 10b, and a corner portion 10c includes a transparent layer 11 as an innermost layer made of quartz glass, a semi-molten layer 13 as an outermost layer made of raw material silica powder solidified in a semi-molten state, and a bubble layer 12 made of quartz glass interposed therebetween. An infrared transmissivity of the corner portion 10c in a state where the semi-molten layer 13
(Continued)

is removed is 25 to 51%, the infrared transmissivity of the corner portion 10*c* in the state where the semi-molten layer 13 is removed is lower than an infrared transmissivity of the side wall portion 10*a*, and the infrared transmissivity of the side wall portion 10*a* in the state where the semi-molten layer 13 is removed is lower than an infrared transmissivity of the bottom portion 10*b*.

7 Claims, 11 Drawing Sheets

(51) Int. Cl.
    *C03C 19/00*     (2006.01)
    *C30B 29/06*     (2006.01)
    *F27B 14/10*     (2006.01)
    *G01N 21/3563*     (2014.01)
    *G01N 33/38*     (2006.01)
    *C03B 19/09*     (2006.01)

(52) U.S. Cl.
    CPC ......... *F27B 14/10* (2013.01); *G01N 21/3563* (2013.01); *G01N 33/386* (2013.01); *C03B 19/095* (2013.01)

(58) Field of Classification Search
    CPC ................ C03C 19/00; C03C 2204/08; C03C 2217/213; C03C 2218/113; C03C 2218/15; C03C 3/06; C03C 4/10; C30B 15/10; C30B 29/06; F27B 14/10; G01N 21/3563; G01N 33/386; Y02P 40/57
    See application file for complete search history.

(56) References Cited

FOREIGN PATENT DOCUMENTS

| | | | | |
|---|---|---|---|---|
| EP | 1024118 | A2 | 8/2000 | |
| JP | H0753295 | A | 2/1995 | |
| JP | H08301693 | A | 11/1996 | |
| JP | 09157082 | A * | 6/1997 | |
| JP | H09157082 | A | 6/1997 | |
| JP | 2000159593 | A * | 6/2000 | ........... C03B 19/095 |
| JP | 2000219593 | A | 8/2000 | |
| JP | 2002326889 | A | 11/2002 | |
| JP | 2004107163 | A | 4/2004 | |
| JP | 2009084114 | A * | 4/2009 | ............. C03C 19/00 |
| JP | 2009084114 | A | 4/2009 | |
| JP | 2010105880 | A | 5/2010 | |
| JP | 2016193809 | A | 11/2016 | |
| JP | 2016193809 | A * | 11/2016 | |
| JP | 2018039702 | A | 3/2018 | |
| JP | 2018043903 | A | 3/2018 | |
| WO | 2020137647 | A1 | 7/2020 | |

OTHER PUBLICATIONS

International Search Report (ISR) dated Feb. 18, 2020, issued for International application No. PCT/JP2019/049119 for a co-pending U.S. Appl. No. 17/413,925. (2 pages).

An Office Action issued by the German Patent Office, dated Jun. 19, 2023, for German related application No. 112019006492.4 (9 pages).

* cited by examiner (a)  (b)

S11 — PREPARE SAMPLE OF CRUCIBLE PIECE

S12 — REMOVE SEMI-MOLTEN LAYER 13 FROM CRUCIBLE PIECE

S13 — MEASURE INFRARED TRANSMITTANCE OF CRUCIBLE PIECE

FIG. 10

| CRUCIBLE SAMPLE | INFRARED TRANSMITTANCE (%) OF CRUCIBLE MEASURED BY REMOVING SEMI-MOLTEN LAYER | | | REDUCTION IN OXYGEN CONCENTRATION ($\leq 12 \times 10^{17}$ atoms/cm$^3$) | OCCURRENCE OF DISLOCATION | OVERALL DETERMINATION |
|---|---|---|---|---|---|---|
| | SIDE WALL PORTION | CORNER PORTION | BOTTOM PORTION | | | |
| #1 (EXAMPLE 1) | 55 | 46 | 52 | SUFFICIENTLY SATISFIED | ABSENT | ○ |
| #2 (EXAMPLE 2) | 70 | 25 | 50 | SUFFICIENTLY SATISFIED | ABSENT | ○ |
| #3 (EXAMPLE 3) | 56 | 33 | 36 | SUFFICIENTLY SATISFIED | ABSENT | ○ |
| #4 (EXAMPLE 4) | 84 | 46 | 57 | SUFFICIENTLY SATISFIED | ABSENT | ○ |
| #5 (EXAMPLE 5) | 52 | 51 | 70 | SATISFIED | ABSENT | ○ |
| #6 (EXAMPLE 6) | 46 | 39 | 51 | SATISFIED | ABSENT | ○ |
| #7 (COMPARATIVE EXAMPLE 1) | 86 | 65 | 59 | NOT SATISFIED | ABSENT | × |
| #8 (COMPARATIVE EXAMPLE 2) | 52 | 58 | 72 | NOT SATISFIED | ABSENT | × |
| #9 (COMPARATIVE EXAMPLE 3) | 56 | 20 | 33 | SUFFICIENTLY SATISFIED | PRESENT | × |
| #10 (COMPARATIVE EXAMPLE 4) | 39 | 24 | 46 | SUFFICIENTLY SATISFIED | PRESENT | × |
| #11 (COMPARATIVE EXAMPLE 5) | 50 | 20 | 40 | SUFFICIENTLY SATISFIED | PRESENT | × |
| #12 (COMPARATIVE EXAMPLE 6) | 50 | 55 | 40 | NOT SATISFIED | ABSENT | × |

FIG. 11

| QUARTZ CRUCIBLE SAMPLE | MEASUREMENT RESULTS (%) OF INFRARED TRANSMITTANCE OF CORNER PORTION | | CRYSTAL OXYGEN CONCENTRATION ($\times 10^{17}$ atoms/cm$^3$) |
|---|---|---|---|
| | BEFORE REMOVING SEMI-MOLTEN LAYER (EVALUATION METHOD OF RELATED ART) | BEFORE REMOVING SEMI-MOLTEN LAYER (EVALUATION METHOD OF PRESENT INVENTION) | |
| A1, A2 | 11 | 26 | 10.5 |
| B1, B2 | 26 | 30 | 10.6 |
| C1, C2 | 25 | 28 | 10.5 |
| D1, D2 | 27 | 36 | 12.3 |
| E1, E2 | 16 | 18 | 8.5 |
| F1, F2 | 36 | 55 | 14.0 |

FIG. 12
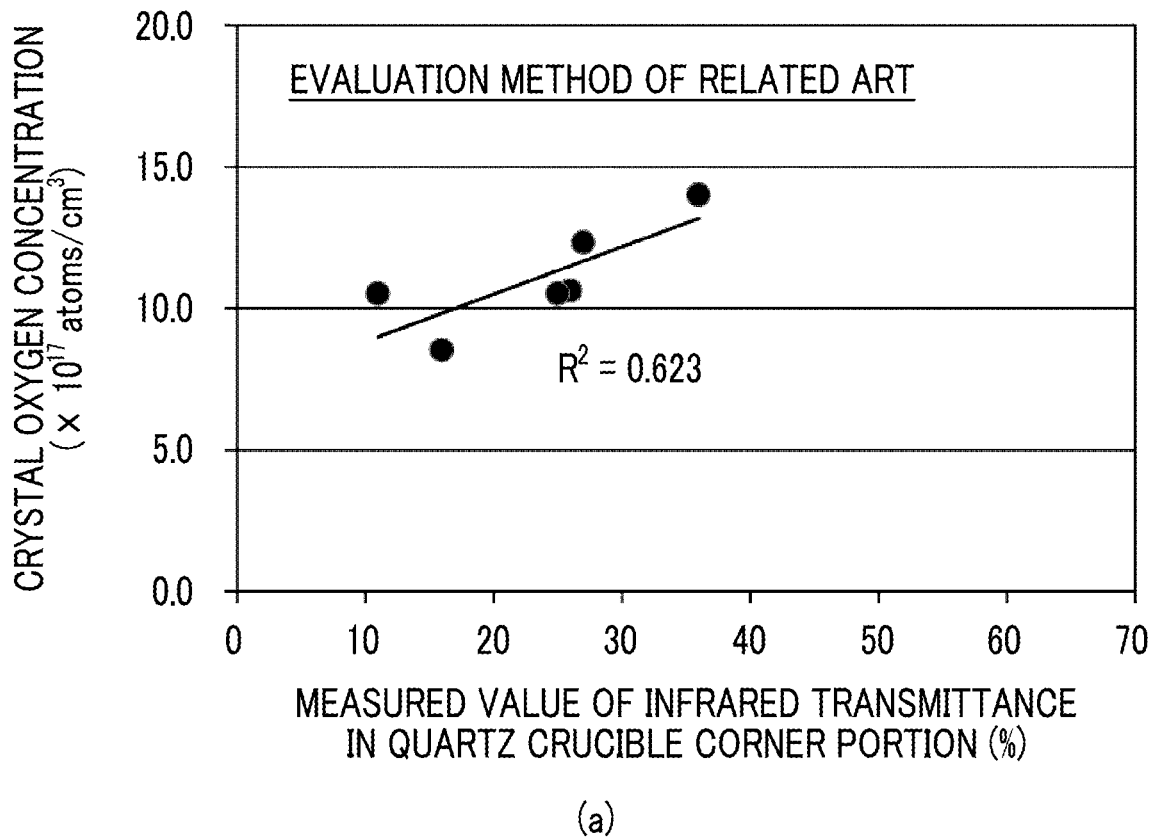
(a)
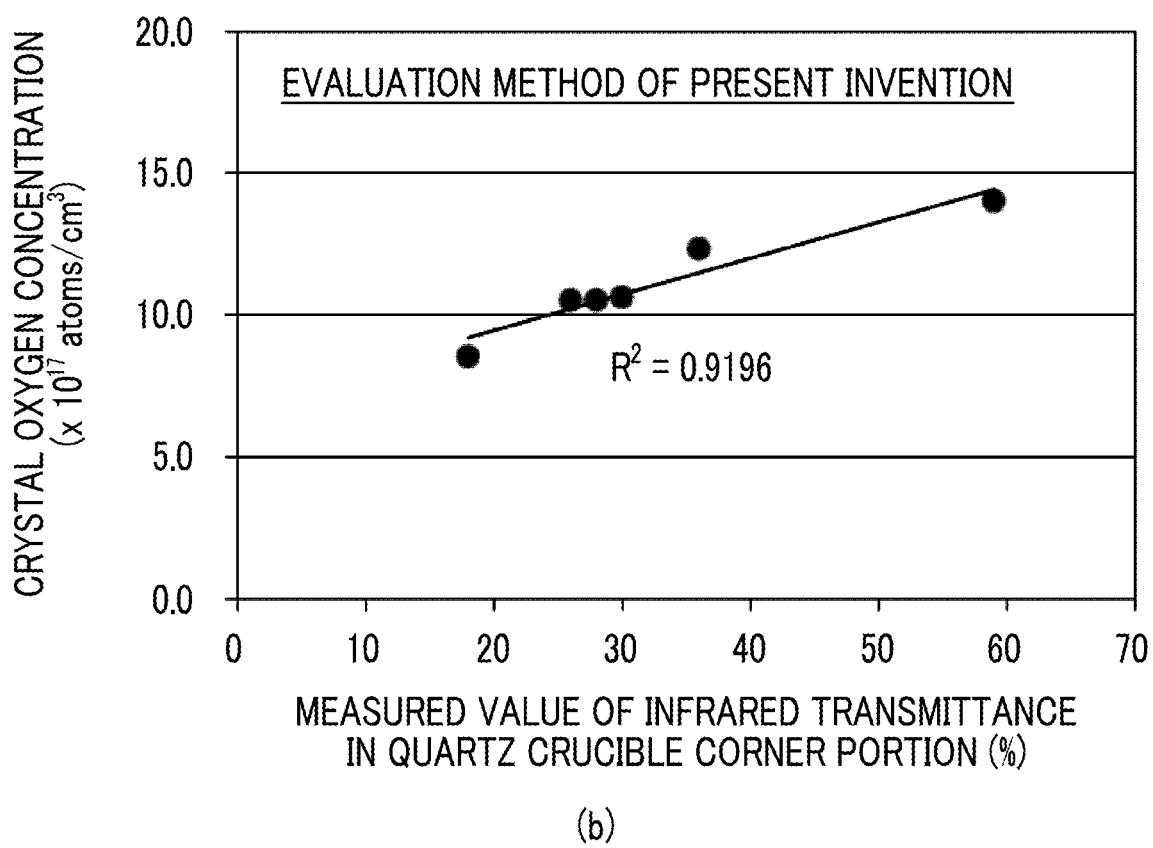
(b)

QUARTZ GLASS CRUCIBLE, MANUFACTURING METHOD OF SILICON SINGLE CRYSTAL USING THE SAME, AND INFRARED TRANSMISSIVITY MEASUREMENT METHOD AND MANUFACTURING METHOD OF QUARTZ GLASS CRUCIBLE

CROSS-REFERENCE TO RELATED APPLICATIONS

This application is the U.S. National Phase under 35 U.S.C. § 371 of International Application PCT/JP2019/049120, filed Dec. 16, 2019, which claims priority to Japanese Patent Application No. JP2018-244361, filed Dec. 27, 2018 and No. 2018-244362, filed Dec. 27, 2018. The International Application was published under PCT Article 21(2) in a language other than English.

TECHNICAL FIELD

The present invention relates to a quartz glass crucible used for manufacturing a silicon single crystal by the Czochralski method (CZ method), and a manufacturing method of a silicon single crystal using the same. The present invention also relates to an infrared transmissivity evaluation method of such a quartz glass crucible and a manufacturing method of a quartz glass crucible using the same.

BACKGROUND ART

A quartz glass crucible is used for manufacturing a silicon single crystal by the CZ method. In the CZ method, a silicon raw material is heated and melted in the quartz glass crucible, a seed crystal is dipped into the silicon melt, and then the seed crystal is gradually pulled up while rotating the crucible to grow a single crystal. In order to manufacture a high-quality silicon single crystal for a semiconductor device at low costs, it is necessary to increase the single crystallization rate in a single pulling-up step. For this, a crucible having a stable shape capable of stably holding the silicon melt and withstanding long-term use is necessary.

Regarding the quartz glass crucible, Patent Literature 1 describes a quartz glass crucible in which the infrared transmissivity of any part including a side wall portion, a curved portion, and a bottom portion of the crucible is 30 to 80% and the average infrared transmissivity of the curved portion is higher than the average infrared transmissivities of the side wall portion and the bottom portion in order to pull up a silicon single crystal having a high single crystallization rate and a large amount of oxygen dissolved. In addition, in Patent Literature 1, it is described that the infrared transmissivity of the crucible also differs depending on the surface roughness, and this surface roughness can be adjusted by the particle size of a quartz powder of the raw material. In a case where the particle size is coarse, the transmissivity decreases, and in a case where the particle size is fine, the transmissivity increases.

In addition, Patent Literature 2 describes a quartz glass crucible in which an infrared transmissivity is 3 to 30%, a thermal conductivity is $3.0 \times 10^{-3}$ to $12.0 \times 10^{-3}$ cal/cm·s·°C., the surface roughness Ra of an outer surface is 2 to 20 μm, and the bubble area of a bubble layer is 0.5 to 5% in order to suppress the molten metal surface vibration of a silicon melt. In particular, it is described that if the state of the formed outer surface of the crucible wall is smooth, scattering of heat rays is suppressed and infrared light is easily transmitted.

Patent Literature 3 describes a quartz glass crucible in which at least a bottom portion of the crucible is opaque and the average roughness Ra of the center line of the entire outer surface of the crucible is set to 0.1 μm to 50 μm in order to improve a single crystallization rate. In addition, Patent Literature 4 describes a quartz glass crucible in which the average roughness Ra of an outer peripheral wall surface is set to 6 to 14 μm and the maximum height Ry thereof is set to 40 to 70 μm in order to improve a DF rate (single crystal pulling-up yield). Furthermore, Patent Literature 5 describes a quartz glass crucible in which a semi-molten quartz layer is formed on the surface of an outer surface layer containing bubbles, the surface roughness Ra of the semi-molten quartz layer is set to 50 to 200 μm, and the layer thickness of the semi-molten layer is set to 0.5 to 2.0 mm.

BACKGROUND ART LITERATURE

Patent Literature

Patent Literature 1: Japanese Patent Application Laid-Open No. Hei-9-157082
Patent Literature 2: Japanese Patent Application Laid-Open No. 2000-219593
Patent Literature 3: Japanese Patent Application Laid-Open No. Hei-7-53295
Patent Literature 4: Japanese Patent Application Laid-Open No. 2004-107163
Patent Literature 5: Japanese Patent Application Laid-Open No. 2009-84114

SUMMARY OF INVENTION

Problems to be Solved by the Invention

During a step of pulling up a silicon single crystal, the inner surface of a quartz glass crucible comes into contact with a silicon melt and is gradually eroded, so that the silicon single crystal manufactured by the CZ method contains oxygen supplied from the crucible. Oxygen in the silicon single crystal not only acts as a gettering site for pollutant metals, but also plays a role in immobilizing dislocations and increasing mechanical strength. However, too high an oxygen concentration not only adversely affects device properties but rather causes a decrease in mechanical strength. In recent years, due to improvements in manufacturing technologies, an improvement in device properties has been emphasized rather than securing a gettering effect. Therefore, a silicon single crystal having a low oxygen concentration, that is, an interstitial oxygen concentration of, for example, $12 \times 10^{17}$ atoms/cm$^3$ or less (Old ASTM_F121 (1979)) is required.

In order to manufacture a silicon single crystal having a low oxygen concentration, it is necessary to suppress the heating temperature of the crucible. For this, it is necessary to adjust the infrared transmissivity of the crucible. However, when the heating temperature is too low, the temperature of the silicon melt decreases, so that it becomes difficult to control crystal pulling-up. Therefore, there is a problem that the single crystallization rate deteriorates.

It should be noted that there are cases where a semi-molten layer is formed on the outer surface of a quartz glass crucible manufactured from silica powder as a raw material. The semi-molten layer is a layer formed of raw material silica powder which is cooled in a partially incompletely melted state, and is an opaque layer having a high surface roughness. Therefore, the infrared transmissivity thereof decreases due to diffused reflection caused by surface irregularities, and the variations in the state of the formed semi-molten layer also increase variation in the infrared transmissivity. On the other hand, the crucible during a crystal pulling-up step reaches a high temperature of 1500° C. or higher, and it is considered that the outer surface of the crucible is smoothed and diffused reflection disappears. In practice, the outer surface of the crucible taken out after pulling-up, cools and hardens in a state of being adapted to the inner surface of a carbon susceptor, and the surface roughness becomes uniform. Therefore, in a case where the infrared transmissivity of the quartz glass crucible is evaluated as it is in the state before use in which the semi-molten layer is formed, it is difficult to accurately control the oxygen concentration in the silicon single crystal based on the evaluation result.

Patent Literatures 1 to 5 disclose the adjustment of an infrared transmissivity by controlling the surface roughness of a crucible and the like. However, all of Patent Literatures 1 to 5 do not consider the effect of a semi-molten layer, and do not adjust the infrared transmissivity by focusing on the actual heat transfer and scattering at the time of pulling-up, and it is difficult to perform precise control of crucible properties required to manufacture a silicon single crystal having a low oxygen concentration.

Therefore, an object of the present invention is to provide a quartz glass crucible capable of increasing the manufacturing yield of a silicon single crystal having a low oxygen concentration, and a manufacturing method of a silicon single crystal using the same. Another object of the present invention is to provide an infrared transmissivity measurement method and a manufacturing method of a quartz glass crucible capable of increasing the manufacturing yield of a silicon single crystal having a desired oxygen concentration.

Means for Solving the Problems

In order to solve the above problems, a quartz glass crucible according to the present invention is a quartz glass crucible including: a cylindrical side wall portion; a bottom portion; a corner portion connecting the side wall portion and the bottom portion to each other; a transparent layer made of quartz glass that does not contain bubbles; a bubble layer formed outside the transparent layer and made of quartz glass containing a large number of bubbles; and a semi-molten layer formed outside the bubble layer and made of raw material silica powder solidified in a semi-molten state, in which an infrared transmissivity of the corner portion in a state where the semi-molten layer is removed is 25 to 51%, the infrared transmissivity of the corner portion in the state where the semi-molten layer is removed is lower than an infrared transmissivity of the side wall portion in the state where the semi-molten layer is removed, and the infrared transmissivity of the corner portion in the state where the semi-molten layer is removed is lower than an infrared transmissivity of the bottom portion in the state where the semi-molten layer is removed.

According to the present invention, it is possible to suppress an excessive heat input from the corner portion of the crucible, suppress erosion of the crucible, and thus suppress the supply of oxygen from the crucible to a silicon melt, so that a silicon single crystal having a low oxygen concentration can be manufactured. In addition, in the present invention, the infrared transmissivity of the crucible can be evaluated in a state close to an actual use state during a crystal pulling-up step, so that the infrared transmissivity of the crucible can be controlled more precisely. Therefore, the manufacturing yield of a silicon single crystal having a low oxygen concentration can be increased.

In the present invention, it is preferable that the infrared transmissivity of the side wall portion in the state where the semi-molten layer is removed is higher than the infrared transmissivity of the bottom portion in the state where the semi-molten layer is removed. In this case, it is preferable that the infrared transmissivity of the side wall portion in the state where the semi-molten layer is removed is 46 to 84%, and the infrared transmissivity of the bottom portion in the state where the semi-molten layer is removed is 36 to 70%. According to this, the manufacturing yield of a silicon single crystal having a low oxygen concentration can be increased. In addition, the silicon melt can be heated while keeping a heater power low at the initial stage of the pulling-up step.

In the present invention, it is preferable that a thermal conductivity of the corner portion in the state where the semi-molten layer is removed is $1.5 \times 10^{-3}$ to $5.8 \times 10^{-3}$ cal/cm·s·° C., the thermal conductivity of the corner portion in the state where the semi-molten layer is removed is lower than a thermal conductivity of the side wall portion in the state where the semi-molten layer is removed, and the thermal conductivity of the corner portion in the state where the semi-molten layer is removed is lower than a thermal conductivity of the bottom portion in the state where the semi-molten layer is removed. In this case, it is preferable that the thermal conductivity of the side wall portion in the state where the semi-molten layer is removed is $3.5 \times 10^{-3}$ to $15.0 \times 10^{-3}$ cal/cm·s·° C., and the thermal conductivity of the bottom portion in the state where the semi-molten layer is removed is $2.7 \times 10^{-3}$ to $13.2 \times 10^{-3}$ cal/cm·s·° C.

In pulling up a silicon single crystal by the CZ method, when the thermal conductivity of the quartz glass crucible is low, an increased amount of heating is required to melt the silicon raw material, and the time required for a melting step of the silicon raw material becomes long. In addition, since the silicon raw material has to be more strongly heated to be melted, the quartz crucible may be deformed due to high temperature. Deformation of the quartz crucible may interfere with the pulling-up of the single crystal. In addition, when the amount of heating of the silicon melt is insufficient, a portion of the melt may be solidified, which may have an adverse effect. On the contrary, when the thermal conductivity of the quartz crucible is high, there are cases where it is difficult to control the diameter of the silicon single crystal during pulling-up. However, in a case where the thermal conductivity of each part of the crucible is at least within the above range, the single crystal can be pulled up without any problem.

In the present invention, it is preferable that a thickness of the bubble layer of the corner portion is 10 to 35 mm, a thickness of the bubble layer of the side wall portion is 1 to 21 mm, and a thickness of the bubble layer of the bottom portion is 4 to 21 mm. With this configuration, it is possible to easily realize a quartz glass crucible in which the infrared transmissivity of each part of the crucible satisfies the above condition in the state where the semi-molten layer is removed.

In addition, a manufacturing method of a silicon single crystal according to the present invention is a manufacturing method of a silicon single crystal by a Czochralski method, including: pulling up a silicon single crystal having an oxygen concentration of $12 \times 10^{17}$ atoms/cm$^3$ or less using the quartz glass crucible according to the present invention.

According to the present invention, the manufacturing yield of a silicon single crystal having a low oxygen concentration can be increased.

In addition, a quartz glass crucible according to the present invention is a quartz glass crucible including: a cylindrical side wall portion; a bottom portion; a corner portion connecting the side wall portion and the bottom portion to each other; a transparent layer made of quartz glass that does not contain bubbles; a bubble layer formed outside the transparent layer and made of quartz glass containing a large number of bubbles; a semi-molten layer formed outside the bubble layer and made of raw material silica powder solidified in a semi-molten state; and at least one semi-molten layer-removed portion formed of a region from which a portion of the semi-molten layer has been removed.

According to the present invention, the infrared transmissivity of the crucible can be evaluated in a state close to an actual use state during a crystal pulling-up step, so that the crucible after the evaluation can be used in an actual crystal pulling-up step.

In the present invention, it is preferable that the semi-molten layer-removed portion includes a first semi-molten layer-removed portion provided in the side wall portion, a second semi-molten layer-removed portion provided in the corner portion, and a third semi-molten layer-removed portion provided in the bottom portion. Accordingly, the infrared transmissivity of each part of the crucible can be evaluated in a state close to an actual use state during a crystal pulling-up step, so that the crucible after the evaluation can be used in an actual crystal pulling-up step.

In addition, an infrared transmissivity measurement method of a quartz glass crucible of the present invention is an infrared transmissivity measurement method of a quartz glass crucible, in which the quartz glass crucible includes a transparent layer made of quartz glass that does not contain bubbles, a bubble layer formed outside the transparent layer and made of quartz glass containing a large number of bubbles, and a semi-molten layer formed outside the bubble layer and made of raw material silica powder solidified in a semi-molten state, the infrared transmissivity measurement method including: a step of processing an outer surface of the quartz glass crucible formed by the semi-molten layer so that a surface roughness of the outer surface becomes low; and a step of measuring an infrared transmissivity of the quartz glass crucible based on infrared light passing through the outer surface after processing the outer surface.

According to the present invention, since the infrared transmissivity is evaluated in a state where the semi-molten layer is removed in the state before use and the individual differences in the semi-molten layer for each crucible are cancelled out, the infrared transmissivity of the crucible can be evaluated in a state close to an actual use state during a crystal pulling-up step, so that the infrared transmissivity of the crucible can be controlled more precisely. Therefore, the manufacturing yield of a silicon single crystal having a low oxygen concentration can be increased.

In the infrared transmissivity measurement method according to the present invention, it is preferable that in the step of processing the outer surface, the outer surface is processed so that an arithmetic average roughness Ra of the outer surface becomes 15 μm or less, and it is particularly preferable that the outer surface is processed until the semi-molten layer is removed. According to this, the infrared transmissivity of the crucible can be evaluated without being affected by the semi-molten layer.

In the infrared transmissivity measurement method according to the present invention, it is preferable that the infrared transmissivity is measured using a crucible piece cut out from the quartz glass crucible. According to this, it is possible to easily process the outer surface of the quartz glass crucible and measure the infrared transmissivity.

In the present invention, it is preferable that the step of processing the outer surface is a polishing treatment or a blasting treatment. According to this method, the outer surface of the quartz glass crucible can be easily processed.

In addition, a manufacturing method of a quartz glass crucible according to the present invention is a manufacturing method of a quartz glass crucible, in which the quartz glass crucible includes a transparent layer made of quartz glass that does not contain bubbles, a bubble layer formed outside the transparent layer and made of quartz glass containing a large number of bubbles, and a semi-molten layer formed outside the bubble layer and made of raw material silica powder solidified in a semi-molten state, the manufacturing method including: a step of manufacturing a first quartz glass crucible based on first manufacturing conditions; a step of processing an outer surface of the first quartz glass crucible formed by the semi-molten layer so that a surface roughness of the outer surface becomes low; after processing the outer surface, a step of measuring an infrared transmissivity of the first quartz glass crucible based on infrared light passing through an outer surface; and a step of manufacturing a second quartz glass crucible based on second manufacturing conditions modified based on a measurement result of the infrared transmissivity of the first quartz glass crucible so that a measured value of the infrared transmissivity becomes a target value.

According to the present invention, the infrared transmissivity of the quartz glass crucible before use can be evaluated in a state close to an actual use state. Therefore, the infrared transmissivity of the crucible during the crystal pulling-up step can be controlled more precisely, and accordingly, for example, the manufacturing yield of a silicon single crystal having a low oxygen concentration can be increased.

Effects of the Invention

According to the present invention, it is possible to provide a quartz glass crucible capable of increasing the manufacturing yield of a silicon single crystal having a low oxygen concentration and a manufacturing method of a silicon single crystal using the same. In addition, according to the present invention, it is possible to provide a manufacturing method of a quartz glass crucible capable of measuring the infrared transmissivity of a quartz glass crucible in a state close to an actual use state, and increasing the manufacturing yield of a silicon single crystal having a low oxygen concentration.

BRIEF DESCRIPTION OF THE DRAWINGS

FIG. 10 is a table showing the infrared transmissivity measured by removing the semi-molten layer of each part of samples #1 to #12 of the quartz glass crucible and the measurement results of the oxygen concentration of a silicon single crystal pulled up using the crucible samples.

FIG. 11 is a table showing the measurement results of the infrared transmissivity of a corner portion of the crucible according to evaluation methods of the related art and the present invention, and the oxygen concentration of a silicon single crystal manufactured by using the crucible.

FIGS. 12 (a) and (b) are a scatter plot and a regression line showing the relationship between the measurement results of the infrared transmissivity of the quartz glass crucible and a crystal oxygen concentration, in which the horizontal axis represents a measured value of the infrared transmissivity, and the vertical axis represents the crystal oxygen concentration.

MODE FOR CARRYING OUT THE INVENTION

Hereinafter, preferred embodiments of the present invention will be described in detail with reference to the accompanying drawings.

Figure 1:
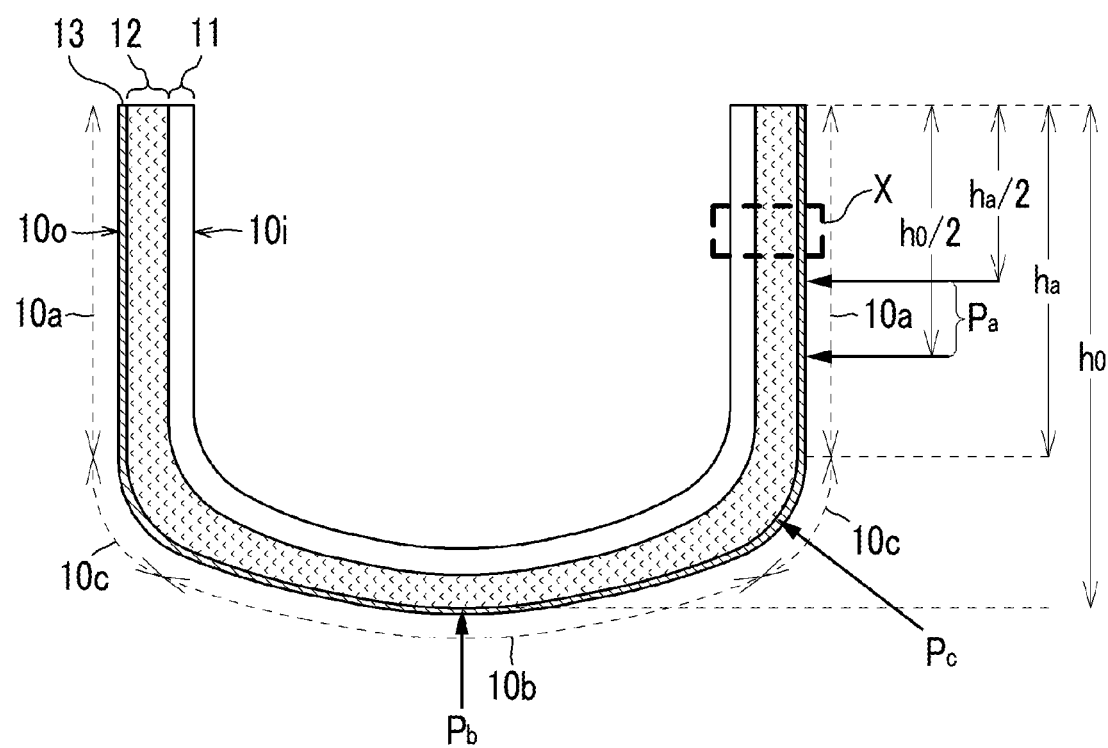
FIG. 1 is a schematic side cross-sectional view illustrating the structure of a quartz glass crucible according to an embodiment of the present invention.
Figure 2:
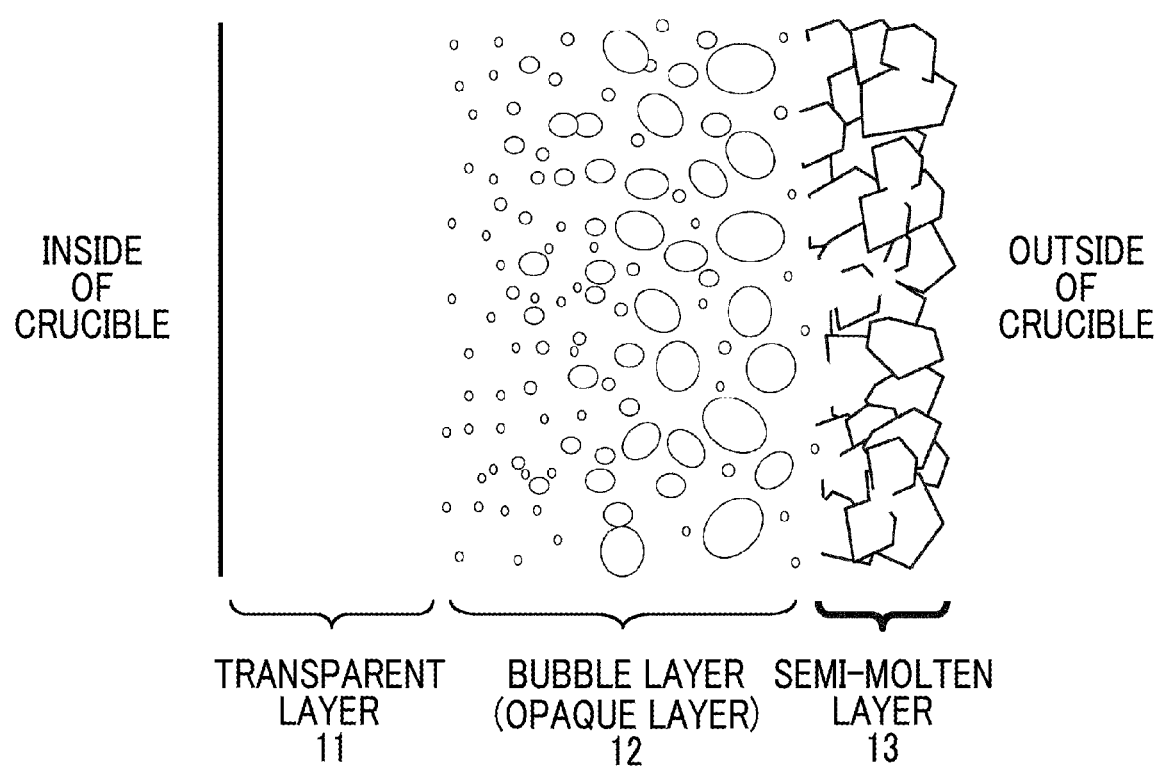
FIG. 2 is an enlarged partial view of the quartz glass crucible in the X portion of FIG. 1.

FIG. 1 is a schematic side cross-sectional view illustrating the structure of a quartz glass crucible according to an embodiment of the present invention. FIG. 2 is a partially enlarged view of the quartz glass crucible in the X portion of FIG. 1.

As illustrated in FIG. 1 and FIG. 2, a quartz glass crucible 1 is a container made of silica glass for supporting a silicon melt, and has a cylindrical side wall portion 10a, a bottom portion 10b, and a corner portion 10c that connects the side wall portion 10a and the bottom portion 10b to each other. The bottom portion 10b is preferably a so-called round bottom that is gently curved, but may also be a so-called flat bottom. The corner portion 10c is located between the side wall portion 10a and the bottom portion 10b, and is a part having a greater curvature than the bottom portion 10b.

The aperture of the quartz glass crucible 1 is preferably 22 inches (about 560 mm) or more, and particularly preferably 32 inches (about 800 mm) or more. This is because such a crucible having a large aperture is used for pulling up a large-size silicon single crystal ingot having a diameter of 300 mm or more, and is required to not affect the quality of the single crystal even when used for a long period of time. In recent years, stabilization of crystal quality has become a problem due to an increase in the size of crucibles and the lengthening of a pulling-up step caused by an increase in the size of silicon single crystals, and stabilization of crystal quality is an extremely important issue for large crucibles. Although the thickness of the crucible slightly varies depending on its part, the thickness of the side wall portion 10a of a crucible of 22 inches or more is preferably 7 mm or more, and the thickness of the side wall portion 10a of a crucible of 24 inches (about 600 mm) or more is preferably 8 mm or more. In addition, the thickness of the side wall portion 10a of a large crucible of 32 inches or more is preferably 10 mm or more, and the thickness of the side wall portion 10a of a large crucible of 40 inches (about 1000 mm) or more is more preferably 13 mm or more.

As illustrated in FIG. 2, the quartz glass crucible 1 includes a transparent layer 11 (bubble-free layer) made of quartz glass containing no bubbles, a bubble layer 12 (opaque layer) which is made of quartz glass containing a large number of minute bubbles and is formed on the outer side of the crucible from the transparent layer 11, and a semi-molten layer 13 which is formed on the outer side of the bubble layer 12 in which the raw material silica powder is solidified in a semi-molten state.

The transparent layer 11 is a layer that forms an inner surface 10i of the crucible that is in contact with a silicon melt, and is provided to prevent a decrease in single crystallization rate due to bubbles in quartz glass. The thickness of the transparent layer 11 is preferably 0.5 to 10 mm, and is set to an appropriate thickness for each part of the crucible so as not to cause the bubble layer 12 to be exposed due to the transparent layer 11 completely disappearing by erosion during a single crystal pulling-up step. Similar to the bubble layer 12, the transparent layer 11 is preferably provided over the entire crucible from the side wall portion 10a to the bottom portion 10b of the crucible. However, in an upper end portion (rim portion) of the crucible that is not in contact with the silicon melt, the formation of the transparent layer 11 can be omitted.

The transparent layer 11 is a part on the inner side of the quartz crucible having a bubble content of 0.1 vol % or less. The expression "the transparent layer 11 contains no bubbles" means that the bubble content and the bubble size are such that the single crystallization rate does not decrease due to the bubbles. This is because there is concern that when bubbles are present in the vicinity of the inner surface of the crucible, the bubbles in the vicinity of the inner surface of the crucible cannot be confined in the quartz glass due to the erosion of the inner surface of the crucible; the bubbles in the quartz glass may burst due to thermal expansion during crystal pulling-up, and crucible fragments (quartz pieces) may delaminate. In a case where crucible fragments released into the melt are carried to the growth interface of the single crystal by convection of the melt and are incorporated into the single crystal, this causes dislocation of the single crystal. In addition, in a case where bubbles released into the melt due to erosion of the inner surface of the crucible float up to a solid/liquid interface and are incorporated into the single crystal, this causes pinholes. The average diameter of bubbles in the transparent layer 11 is preferably 100 μm or less.

The bubble content of the transparent layer 11 and the diameter of the bubbles can be measured nondestructively using optical detecting means by the method disclosed in Japanese Patent Application Laid-Open No. 2012-116713. The optical detecting means includes a light-receiving device which receives transmitted light or reflected light of the light irradiating the crucible. Light-emitting means of the irradiation light may be built in the light-receiving device, or external light-emitting means may also be used. In addition, as the optical detecting means, one that can be turned along the inner surface of the crucible is preferably used. As the irradiation light-emitting means, X-rays, laser light, and the like, as well as visible light, ultraviolet light, and infrared light can be used. As the light-receiving device, a digital camera including an optical lens and an imaging element can be used. Measurement results obtained by the optical detecting means are received by an image processing device to calculate the diameter of bubbles and the bubble content per unit volume.

In order to detect bubbles present at a certain depth from the surface of the crucible, the focal point of the optical lens may be scanned from the surface in the depth direction. Specifically, an image of the inner surface of the crucible is taken using the digital camera, the inner surface of the crucible is divided into predetermined areas to obtain a reference area S1, an area S2 occupied by bubbles is obtained for each reference area S1, and an area bubble content Ps=(S2/S1)×100(%) is calculated.

In the calculation of the bubble content by the volume ratio, a reference volume V1 is obtained from the depth at which the image is taken and the reference area S1. Furthermore, a bubble is regarded as a spherical shape, and a volume V2 of the bubble is calculated from the diameter of the bubble. A volume bubble content Pv=(V2/V1)×100(%) is calculated from V1 and V2. In the present invention, the volume bubble content Pv is defined as "bubble content". An arithmetic average value obtained from the diameters of the bubbles calculated by regarding the bubble as a sphere is defined as the "average diameter of the bubbles".

It should be noted that the reference volume is 5 mm×5 mm×depth 0.45 mm, the minimum bubble diameter to be measured is 5 μm (those having a diameter of less than 5 μm are ignored), and a resolution may be set such that bubbles having a diameter of 5 μm can be measured. The focal length of the optical lens is shifted in the depth direction of the reference volume V1, the bubbles contained inside the reference volume are captured, and the diameter of the bubbles is measured.

The bubble layer 12 is a layer forming an outer surface 10o of the crucible, and is provided to enhance the heat retention of the silicon melt in the crucible, and heat the silicon melt in the crucible as uniformly as possible by dispersing radiant heat from a heater provided to surround the crucible in a single crystal pulling-up apparatus. Therefore, the bubble layer 12 is provided over the entire crucible from the side wall portion 10a to the bottom portion 10b of the crucible. The thickness of the bubble layer 12 is a value obtained by subtracting the thickness of the transparent layer 11 and the semi-molten layer 13 from the thickness of the crucible wall, and varies depending on the part of the crucible. The bubble content of the bubble layer 12 can be obtained, for example, by specific gravity measurement (Archimedes' method) of an opaque quartz glass piece cut out from the crucible.

The bubble content of the bubble layer 12 is higher than that of the transparent layer 11, preferably more than 0.1 vol % and 5 vol % or less, and more preferably 1 vol % or more and 4 vol % or less. This is because when the bubble content of the bubble layer 12 is 0.1 vol % or less, the function of the bubble layer 12 cannot be manifested, and heat retention becomes insufficient. Furthermore, in a case where the bubble content of the bubble layer 12 exceeds 5 vol %, there is concern that the crucible may be greatly deformed due to expansion of the bubbles, and the single crystal yield may decrease, which causes further insufficient heat transfer properties. In particular, when the bubble content of the bubble layer 12 is 1 to 4%, the balance between heat retention and heat transfer properties is good and preferable. A large number of bubbles contained in the bubble layer 12 can be visually recognized. It should be noted that the above-mentioned bubble content is a value obtained by measuring the crucible before use in a room temperature environment.

The semi-molten layer 13 is a layer formed of silica powder as the raw material of the crucible, which is cooled in a partially incompletely melted state (semi-molten state) in the outer surface of the quartz glass crucible. The semi-molten layer 13 has a rugged surface, greatly scatters and reflects light incident from the outer surface side of the crucible, and thus affects the infrared transmissivity of the crucible. The semi-molten layer 13 is a layer formed in a manufacturing process of the crucible and is not necessarily a layer necessary for pulling up a single crystal. However, since there is no positive reason for removing the semi-molten layer 13, a crucible product is provided in a state in which the semi-molten layer 13 is present. The general thickness of the semi-molten layer 13 formed on the outer surface of the quartz glass crucible is 0.05 to 2.0 mm. The thickness of the semi-molten layer 13 becomes thinner as the temperature gradient near the outer surface of the crucible becomes steeper and becomes thicker as the temperature gradient becomes gentler during the manufacturing of the crucible. The thicker the semi-molten layer 13, the larger the surface roughness, and the more easily the quartz powder is dissociated. Furthermore, since the temperature gradient is different for each part of the crucible, the thickness of the semi-molten layer 13 differs for each part of the crucible.

Whether or not the semi-molten layer 13 is formed on the outer surface of the crucible can be determined by whether or not an amorphous-specific halo pattern in which a diffraction image is blurred and a peak showing crystallinity when the outer surface of the crucible is measured by an X-ray diffraction method coexist. For example, in a case where a measurement target is a crystal layer, a peak showing crystallinity is detected, but a halo pattern in which a diffraction image is blurred is not detected. On the contrary, in a case where a measurement target is a non-crystal layer (amorphous layer), a halo pattern in which a diffraction image is blurred is detected, and a peak showing crystallinity is not detected. When the semi-molten layer 13 formed on the outer surface of the crucible is removed, the surface of the glass is exposed, so that no peak is detected by the X-ray diffraction method. As described above, it can be said that the semi-molten layer is a layer in which a halo pattern in which a diffraction image is blurred and a peak showing crystallinity coexist when measured by the X-ray diffraction method. Furthermore, it can be said that the crystal layer is a layer in which a peak is detected by the X-ray diffraction method, and the non-crystal layer is a layer in which a halo pattern in which a diffraction image is blurred is detected.

In order to prevent contamination of the silicon melt, it is desirable that the quartz glass forming the transparent layer 11 has high purity. Therefore, the quartz glass crucible according to the present embodiment preferably includes two layers, an inner surface layer formed from synthetic silica powder (hereinafter, referred to as "synthetic layer") and an outer surface layer formed from natural silica powder (hereinafter, referred to as "natural layer"). The synthetic silica powder can be manufactured by vapor phase oxidation of silicon tetrachloride ($SiCl_4$) (dry synthesis method) or hydrolysis of silicon alkoxide (sol-gel method). The natural silica powder is silica powder manufactured by pulverizing into particles a natural mineral containing a-quartz as a primary component.

As will be described in detail later, the two-layer structure of the synthetic layer and the natural layer can be manufactured by depositing the natural silica powder along the inner surface of a mold for manufacturing a crucible, depositing the synthetic silica powder thereon, and melting the silica particles by Joule heat through arc discharge. In an initial stage of the arc melting step, the transparent layer 11 is formed by removing bubbles through strong evacuation from the outside of the deposition layers of the silica particles. Thereafter, the evacuation is stopped or weakened, whereby the bubble layer 12 is formed outside the transparent layer 11. For this reason, although the boundary surface between the synthetic layer and the natural layer does not always coincide with the boundary surface between the transparent layer 11 and the bubble layer 12, like the transparent layer 11, the synthetic layer preferably has a thickness that does not completely disappear by erosion of the inner surface of the crucible during the crystal pulling-up step.

Next, the features of the quartz glass crucible according to the present embodiment will be described.

In a case where the quartz glass crucible is divided into three regions, the side wall portion 10a, the corner portion 10c, and the bottom portion 10b, the infrared transmissivity of the corner portion 10c has a larger effect on the oxygen concentration of the silicon single crystal than the infrared transmissivity of the other regions. The reason for this is that the infrared transmissivity of the corner portion 10c affects a heat input from the corner portion 10c, affects the temperature of the inner surface of the crucible, and as a result, affects the amount of oxygen supplied into the silicon melt.

In the present embodiment, the infrared transmissivity of the corner portion 10c of the quartz glass crucible 1 is lower than the infrared transmissivity of the side wall portion 10a, and lower than the infrared transmissivity of the bottom portion 10b. In a case where the quartz glass crucible is divided into three regions, the side wall portion 10a, the corner portion 10c, and the bottom portion 10b, the infrared transmissivity of the corner portion 10c is minimized, thereby suppressing the heat input from the corner portion 10c and suppressing a temperature rise in the inner surface of the crucible. Therefore, the amount of oxygen supplied into the silicon melt can be suppressed, and thus a silicon single crystal having a low oxygen concentration can be grown.

As described above, the semi-molten layer 13 is formed on the outer surface of the quartz glass crucible 1, but the preferable range of the infrared transmissivity of each part of the crucible shown below is a measured value in a state where the semi-molten layer 13 is removed. The reason for such measurement is as follows.

Figure 3:
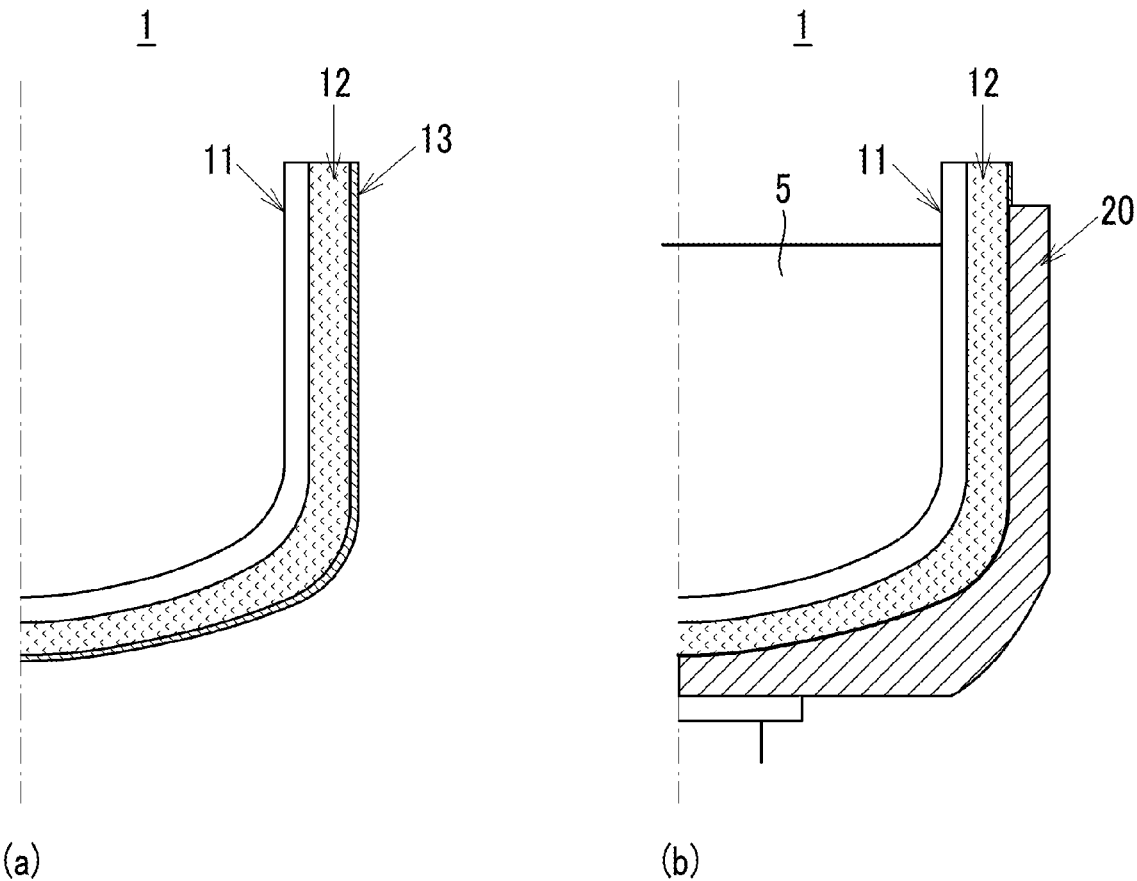
FIGS. 3 (*a*) and (*b*) are diagrams for describing a change in the state of a semi-molten layer of the quartz glass crucible, in which FIG. 3 (*a*) illustrates a state before use, and FIG. 3 (*b*) illustrates a state during use, respectively.

FIGS. 3 (a) and (b) are diagrams for describing a change in the state of the semi-molten layer 13 of the quartz glass crucible 1, in which FIG. 3 (a) illustrates a state before use, and FIG. 3 (b) illustrates a state during use, respectively.

As illustrated in FIG. 3 (a), the semi-molten layer 13 is formed in the quartz glass crucible 1 in a product state before use. As described above, the semi-molten layer 13 is a layer solidified in a state where the raw material silica powder is partially incompletely melted, and the surface state thereof slightly varies for each crucible product depending on the difference in the particle size distribution and the melting conditions of the raw material silica powder, so that infrared transmissivity also varies individually. Furthermore, differences in the surface state of the crucible also occur in each part of the crucible such as the side wall portion 10a, the corner portion 10c, and the bottom portion 10b. When such a crucible is installed in a carbon susceptor and actually used at a high temperature, the state of the semi-molten layer 13 changes.

That is, as illustrated in FIG. 3 (b), the quartz glass crucible 1 is softened by a high temperature of 1500° C. or higher during the single crystal pulling-up step, and a liquid pressure that pushes the crucible wall outward is generated by the silicon melt 5 stored in the crucible. On the other hand, since a carbon susceptor 20 is provided outside the quartz glass crucible 1 and the outer surface of the crucible is constrained in the radial direction, the irregularities of the semi-molten layer 13 are crushed and smoothed. Therefore, the infrared transmissivity of the quartz glass crucible during the single crystal pulling-up step is different from that in a pre-used product state.

Usually, the measurement data of an unused crucible is used to evaluate the quality of the quartz glass crucible. However, as described above, since the irregularities of the outer surface of the crucible are canceled out during use, it is not desirable that the crucible is evaluated based on infrared transmissivity measured in a state where the irregularities of the outer surface differ for each crucible and each part. For example, in a case where the semi-molten layer 13 is present, even if the infrared transmissivity of the crucible is very low, in a case where the infrared transmissivity is high when the semi-molten layer ceases to exist in an actual pulling-up step, a heat input from the outside of the crucible cannot be suppressed, and the oxygen concentration in the single crystal cannot be lowered.

For the above reasons, in the present invention, the semi-molten layer 13 on the outer surface is intentionally removed to reduce the effect of the irregularities of the outer surface on infrared transmissivity, and then the infrared transmissivity of each part of the crucible is measured and evaluated. That is, the present invention simulates the state during use, particularly the state of the semi-molten layer 13 during use of the crucible with respect to the quartz glass crucible before use, and the infrared transmissivity and the distribution of thermal conductivity measured in such a state have the following features. It should be noted that the infrared transmissivity of the quartz glass crucible during the crystal pulling-up step is affected by bubbles that have been thermally expanded at a high temperature, but even the bubbles before the thermal expansion are effective as an evaluation index of infrared transmissivity.

First, in a state where the semi-molten layer 13 is removed, the infrared transmissivity of the corner portion 10c is preferably 25 to 51%, and the thermal conductivity of the corner portion 10c is preferably $1.5 \times 10^{-3}$ to $5.8 \times 10^{-3}$ cal/cm·s·° C. This is because in a case where the infrared transmissivity of the corner portion 10c is lower than 25%, the amount of heating of the silicon melt in the crucible is insufficient, it becomes difficult to control the crystal pulling-up, and dislocations are likely to be formed in the single crystal, while in a case where the infrared transmissivity is higher than 51%, a silicon single crystal having a low oxygen concentration of $12 \times 10^{17}$ atoms/cm$^3$ or less cannot be stably pulled up over its entire length.

Furthermore, in the state where the semi-molten layer 13 is removed, the infrared transmissivity of the side wall portion 10a is preferably 46 to 84%, and the thermal conductivity of the side wall portion 10a is preferably $3.5 \times 10^{-3}$ to $15.0 \times 10^{-3}$ cal/cm·s·° C. By relatively increasing the infrared transmissivity of the side wall portion 10a of the crucible, a heater power at the initial stage of pulling-up can be kept low, thereby suppressing a temperature rise in the inner surface of the corner portion 10c of the crucible and suppressing dissolution of oxygen into the silicon melt. Therefore, it becomes possible to pull up a silicon single crystal having a low oxygen concentration.

In the state where the semi-molten layer 13 is removed, the infrared transmissivity of the bottom portion 10b is 36 to 70%, and the thermal conductivity of the bottom portion 10b is preferably $2.7 \times 10^{-3}$ to $13.2 \times 10^{-3}$ cal/cm·s·° C. By setting the infrared transmissivity of the bottom portion 10b to be equal to or lower than the infrared transmissivity of the side wall portion 10a, it is possible to stabilize the temperature of the silicon melt in the latter half of the pulling-up, thereby stabilizing the oxygen concentration in the silicon single crystal.

A laser flash method can be used to measure thermal conductivity. The laser flash method is a non-contact measurement method by optical heating and optical observation, and measurement time is short. In addition, the laser flash method is a method that enables measurement regardless of the kind of material such as an insulator, semiconductor, and metal, and is widely used because of its wide range of application and simplicity. In the laser flash method, the surface of a flat plate-shaped solid sample installed under adiabatic vacuum is uniformly heated by a pulse laser, and the subsequent diffusion of heat in the thickness direction is observed as the time dependent temperature on the rear surface of the sample, whereby the thermal diffusivity of the flat plate-shaped sample in the thickness direction can be obtained. By multiplying the thermal diffusivity measured by the laser flash method by the specific heat and density of the sample measured by another device, the thermal conductivity can be calculated.

The above infrared transmissivity and thermal conductivity are values measured at room temperature and are values in the thickness direction of the crucible. It should be noted that infrared transmissivity and thermal conductivity of the quartz glass crucible at room temperature are different from the values in a high temperature environment (about 1800° C.) at the time of crystal pulling-up. However, within the above ranges of infrared transmissivity and thermal conductivity at room temperature, a silicon single crystal having a low oxygen concentration can be obtained with a high manufacturing yield.

The thickness of the side wall portion 10a is generally constant from the upper end to the lower end. However, the thickness of the upper end portion is slightly thinner than the average thickness, and the thickness of the lower end portion tends to be slightly thicker than the average thickness. Therefore, infrared transmissivity also changes depending on the position of the side wall portion. Therefore, the measurement position Pa of the thickness and the infrared transmissivity in the side wall portion 10a is preferably measured at a position where the average thickness and the average infrared transmissivity of the side wall portion 10a can be obtained, and is preferably in a range from a position $h_a/2$ of half the height $h_a$ of the side wall portion 10a of the crucible to a position $h_0/2$ of half the height $h_0$ of the entire crucible. In addition, the measurement position Pc of the thickness and infrared transmissivity in the corner portion 10c is preferably the maximum thickness position of the corner portion 10c, and the measurement position Pb of the thickness and infrared transmissivity in the bottom portion 10b is preferably the center of the bottom portion 10b.

The infrared transmissivity of each part of the crucible can be adjusted by changing the thickness of the bubble layer 12. The thickness of the bubble layer 12 is a value obtained by subtracting the thickness of the transparent layer 11 from the thickness of the crucible. When the thickness of the transparent layer 11 is constant, as the thickness of the crucible increases, the thickness of the bubble layer 12 also increases. Therefore, for example, by increasing the thickness of the corner portion 10c to increase the thickness of the bubble layer 12, infrared transmissivity of the corner portion 10c can be lowered.

As a method of partially increasing the thickness of the crucible, in a rotational molding method described later, for example, the following method is included, in which the thickness of a portion of a deposition layer of the raw material silica powder is increased, and the duration and the amount of heating of arc melting are increased at the portion, thereby increasing the thickness of a molten glass thereat. In addition, the bubble layer 12 can be thickened by changing the ratio between the thicknesses of the transparent layer and the bubble layer 12 without increasing the thickness of the crucible. In this case, the thickness of the bubble layer 12 can be made relatively thicker than that of the transparent layer 11 by shortening the time for strongly suctioning air from the outside of the deposition layer of the silica powder. In particular, the ratio of the thickness of the transparent layer and the bubble layer 12 can be partially changed by partially changing the suction force.

Infrared transmissivity of each part of the crucible may be adjusted by changing the bubble content of the bubble layer 12. For example, infrared transmissivity of the corner portion 10c can be lowered by further increasing the bubble content of the bubble layer 12 of the corner portion 10c while keeping the thickness of the bubble layer 12 constant. The bubble content of the bubble layer 12 can be controlled by adjusting the particle size of the raw material silica powder and the temperature at the time of arc heating when the quartz glass crucible 1 is manufactured by the so-called rotational molding method.

As described above, in the quartz glass crucible 1 according to the present embodiment, infrared transmissivity of the corner portion 10c is suppressed to be lower than that in the related art, and infrared transmissivity of the corner portion 10c is lower than that of the side wall portion 10a and the bottom portion 10b. Therefore, the amount of oxygen supplied to the silicon melt can be suppressed to a low level, and a reduction in the amount of oxygen of the silicon single crystal can be achieved.

Figure 4:
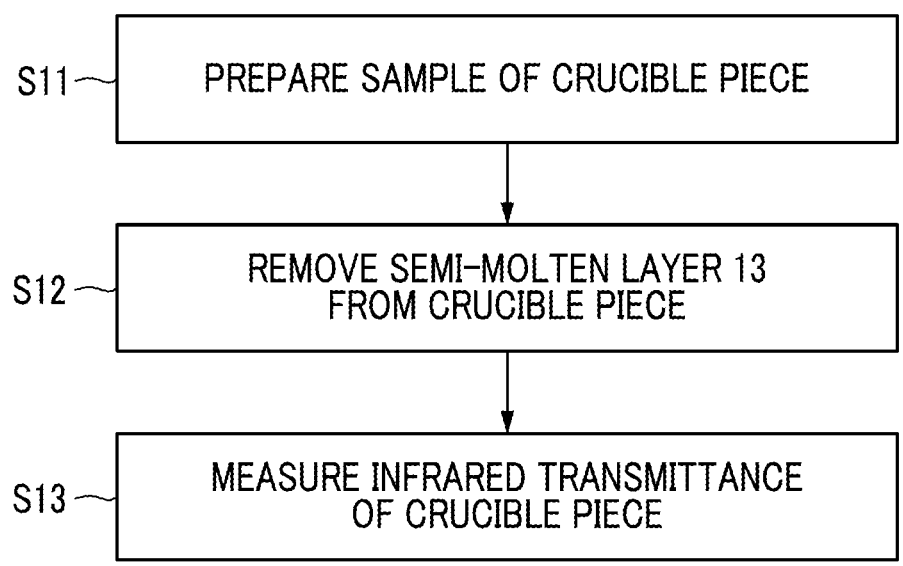
FIG. 4 is a flowchart showing a measurement method of an infrared transmittance of a quartz glass crucible.

FIG. 4 is a flowchart showing an infrared transmissivity measurement method of a quartz glass crucible using a piece of a crucible. In addition, FIG. 5 is a schematic view showing the infrared transmissivity measurement method of a quartz glass crucible.

Figure 5:
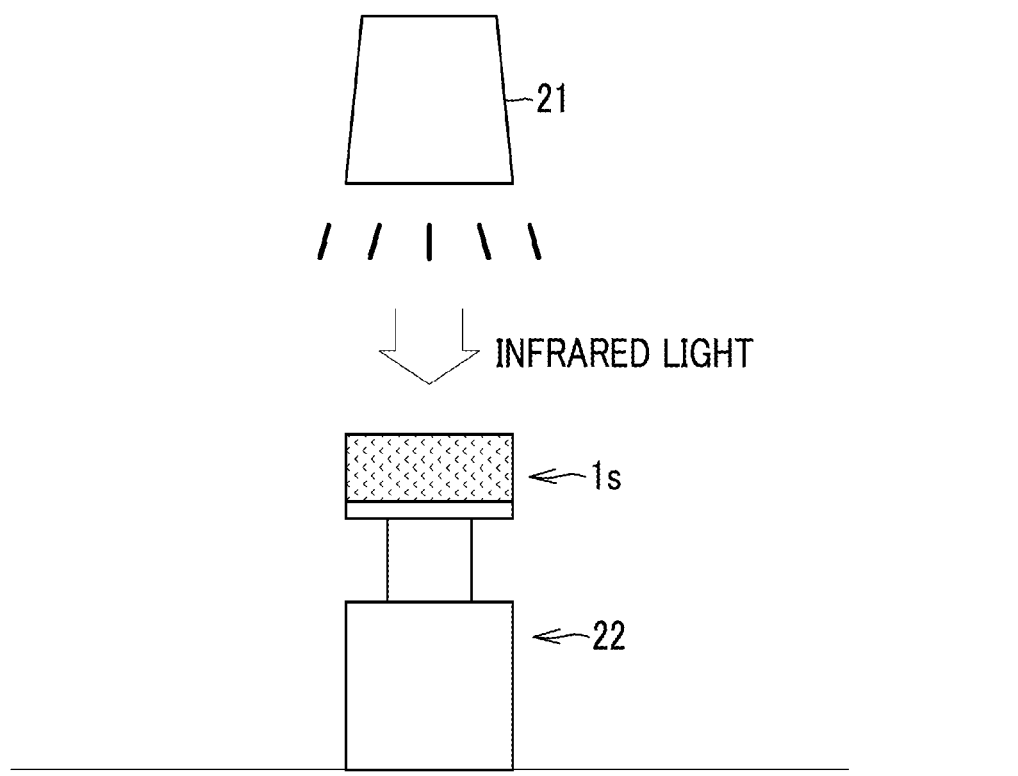
FIG. 5 is a schematic view showing a measurement method of an infrared transmittance of a quartz glass crucible.

As shown in FIG. 4 and FIG. 5, in the measurement of the infrared transmissivity of the quartz glass crucible, first, a sample of a crucible piece cut out from the quartz glass crucible is prepared (step S11). As described above, the quartz glass crucible 1 which is the measurement target has the transparent layer 11, the bubble layer 12 formed outside the transparent layer 11, and the semi-molten layer 13 formed outside the bubble layer 12.

Next, the semi-molten layer 13 is removed from the piece of the crucible (step S12). As a method of removing the semi-molten layer 13, there are a polishing treatment and a blasting treatment, but other methods may also be used. The semi-molten layer 13 is preferably completely removed, but may not be completely removed. It is sufficient that the piece of the crucible is processed so that the surface roughness of the outer surface of the crucible on which the semi-molten layer 13 is formed becomes low to some extent. In this case, the arithmetic average roughness Ra of the outer surface of the crucible is preferably 15 μm or less, and particularly preferably 10 μm or less. As described above, by processing the piece of the crucible so that the surface roughness of the outer surface of the piece of the crucible becomes low, it is possible to appropriately evaluate infrared transmissivity.

Next, infrared transmissivity of the piece of the crucible is measured (step S13). As shown in FIG. 5, in the measurement of infrared transmissivity of a piece of the crucible 1s, a laser power meter 22 (light-receiving device) is disposed below an infrared lamp 21, and the piece of the crucible 1s is disposed on the light-receiving portion of the laser power meter 22. The infrared light from the infrared lamp 21 passes through the piece of the crucible 1s and is received by the laser power meter 22. The infrared transmissivity of the piece of the crucible 1s is obtained as the ratio of the amount of emitted light to the amount of incident light in a case where infrared light is incident from one surface of the crucible wall and the light emitted from the opposite surface is received.

Figure 6:
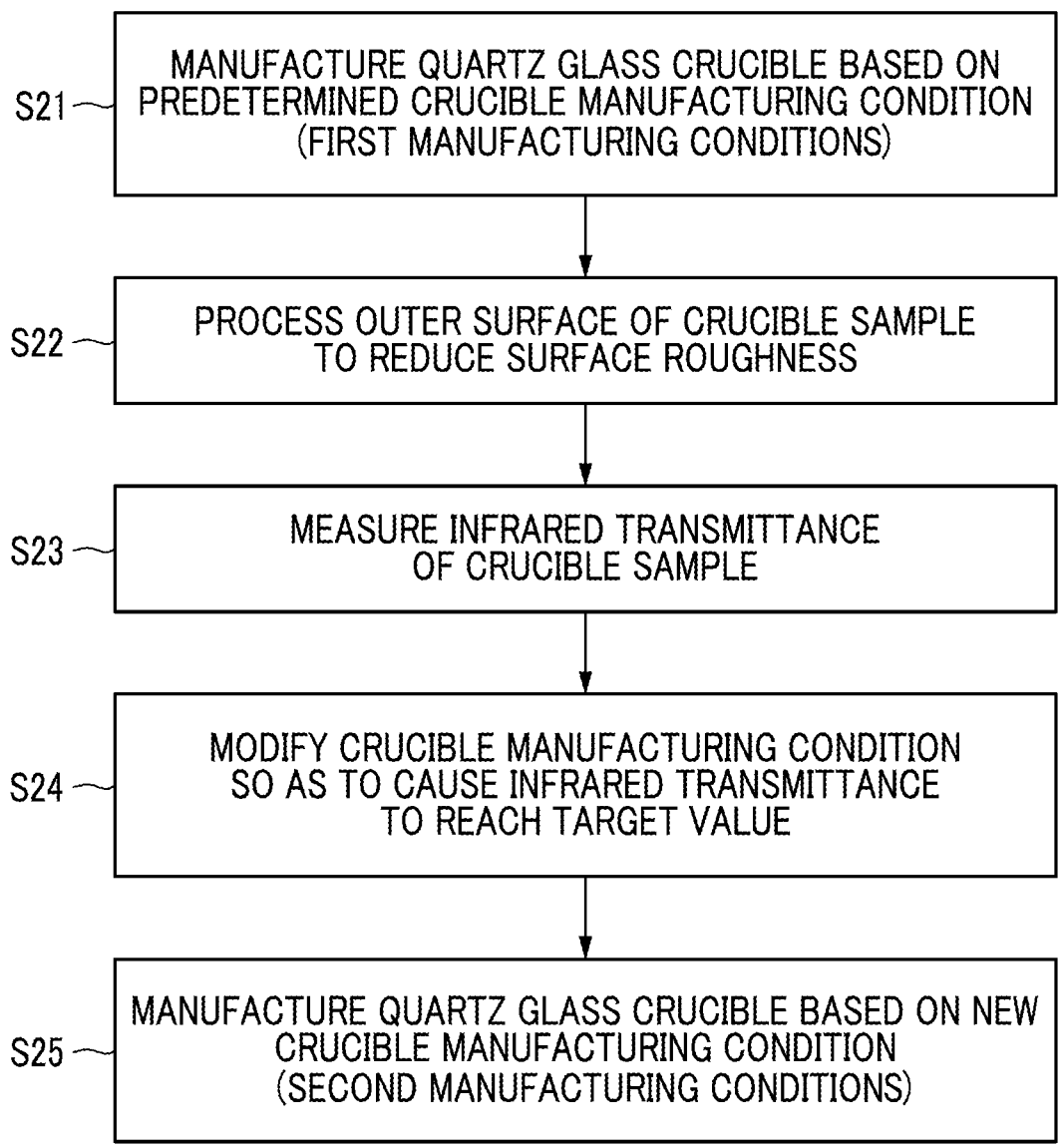
FIG. 6 is a flowchart showing a manufacturing method of a quartz glass crucible including an evaluation method of the infrared transmissivity described above.

FIG. 6 is a flowchart showing a manufacturing method of the quartz glass crucible 1 including the evaluation method of infrared transmissivity described above.

The manufacturing method of the quartz glass crucible 1 according to the present embodiment includes a step (step S21) of manufacturing a quartz glass crucible (first quartz glass crucible) based on predetermined crucible manufacturing conditions (first manufacturing conditions), a step (step S22) of removing the semi-molten layer 13 of the quartz glass crucible, a step (step S23) of measuring infrared transmissivity of the portion of the quartz glass crucible from which the semi-molten layer has been removed, a step (step S24) of modifying the predetermined crucible manufacturing conditions so as to cause a measured value of infrared transmissivity to reach a target value, and a step (step S25) of manufacturing a subsequent quartz glass crucible (second quartz glass crucible) based on new crucible manufacturing conditions (second manufacturing conditions). It should be noted that in the step of removing the semi-molten layer 13, it is not necessary to completely remove the semi-molten layer 13, and it is sufficient to process the outer surface so that the surface roughness becomes low. As described above, by feeding back the evaluation result of infrared transmissivity of the crucible to the crucible manufacturing conditions, it is possible to efficiently manufacture a quartz glass crucible having a desired infrared transmissivity for each part.

Next, the manufacturing method of the quartz glass crucible 1 will be described.

Figure 7:
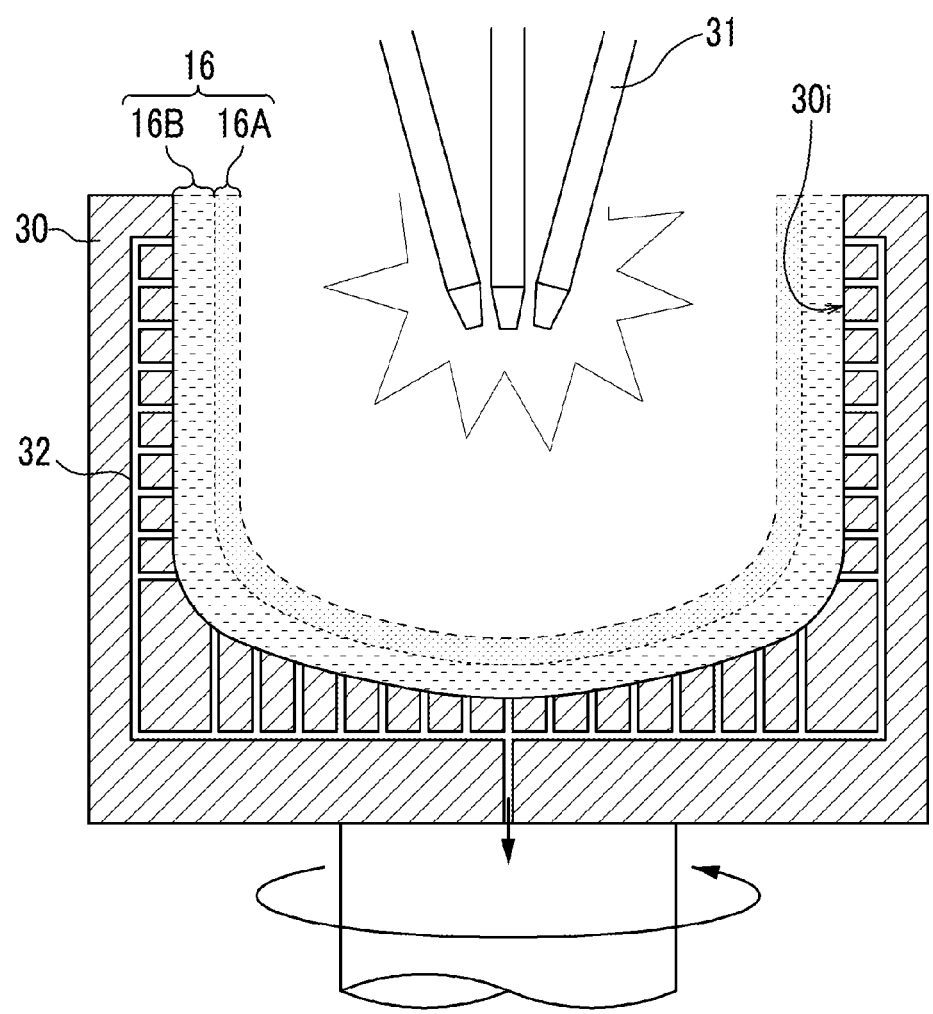
FIG. 7 is a schematic view for describing the manufacturing method of a quartz glass crucible according to a rotational molding method.

FIG. 7 is a schematic view for describing the manufacturing method of the quartz glass crucible 1 according to the rotational molding method.

As illustrated in FIG. 7, the quartz glass crucible 1 according to the present embodiment can be manufactured by the so-called rotational molding method. In the rotational molding method, natural silica powder 16B and synthetic silica powder 16A are sequentially deposited on an inner surface 30i of a rotating mold 30 to form a deposition layer 16 of the raw material silica powder. It is also possible to use only natural silica powder as the raw material of the crucible. This raw material silica powder remains in a certain position while being adhered to the inner surface 30i of the mold 30 by centrifugal force, and is maintained in the shape of the crucible.

Next, an arc electrode 31 is installed in the mold 30, and the deposition layer 16 of the raw material silica powder is arc-melted from the inner surface 30i side of the mold 30. Specific conditions such as heating time and heating temperature need to be appropriately determined in consideration of conditions such as the raw materials and size of the crucible. In this case, the amount of bubbles in the melted quartz glass is controlled by suctioning the deposition layer 16 of the raw material silica powder from a large number of vent holes 32 provided on the inner surface 30i of the mold 30. Specifically, at the start of arc melting, the suction force from the large number of vent holes 32 provided on the inner surface 30i of the mold 30 is strengthened to form the transparent layer 11, and after the formation of the transparent layer 11, the suction force is weakened to form the bubble layer 12.

Since the arc heat is gradually transferred from the inner side to the outer side of the deposition layer 16 of the raw material silica powder to melt the raw material silica powder, by changing decompression conditions at the timing at which the raw material silica powder starts to melt, the transparent layer 11 and the bubble layer 12 can be separately formed. When decompression melting is performed to strengthen decompression at the timing at which the silica powder melts, the arc atmosphere gas is not confined in the glass, and quartz glass containing no bubbles is formed. In addition, when normal melting (atmospheric pressure melting) in which decompression is weakened at the timing at which the silica powder melts, the arc atmosphere gas is confined in the glass and quartz glass containing a large number of bubbles is formed. The thicknesses of the transparent layer 11 and the bubble layer 12 can be adjusted for each part by, for example, changing the disposition and current of the arc electrode 31 to partially change the extent of melting during decompression melting or normal melting.

Thereafter, the arc heating is stopped and the crucible is cooled. Accordingly, the quartz glass crucible 1 in which the transparent layer 11 and the bubble layer 12 are sequentially provided from the inside to the outside of the crucible wall and the semi-molten layer 13 is further formed on the surface of the bubble layer 12 (outer surface of the crucible) is completed (see FIG. 1). As described above, since the semi-molten layer 13 is formed on the outer surface of the quartz glass crucible 1 of a final product, infrared transmissivity is greatly reduced and greatly varies for individual crucibles and for each part. However, by measuring infrared transmissivity of the crucible in the state where the semi-molten layer 13 is removed, it is possible to evaluate the crucible according to an actual use state. Therefore, infrared transmissivity of the crucible during the crystal pulling-up step can be controlled more precisely, whereby the manufacturing yield of the silicon single crystal having the desired oxygen concentration can be increased.

As described above, in the quartz glass crucible 1 according to the present embodiment, since infrared transmissivity of the corner portion in the state where the semi-molten layer is removed is 25 to 51% and is lower than infrared transmissivities of the side wall portion and the bottom portion in the state where the semi-molten layer is removed, it is possible to suppress an excessive heat input from the corner portion of the crucible, suppress erosion of the crucible, and thus suppress the supply of oxygen from the crucible to the silicon melt, so that a silicon single crystal having a low oxygen concentration can be manufactured. In addition, since infrared transmissivity of the crucible is evaluated in a state close to the actual use state, infrared transmissivity of the crucible during the crystal pulling-up step can be controlled more precisely, and accordingly, the manufacturing yield of a silicon single crystal having a low oxygen concentration can be increased.

Figure 8:
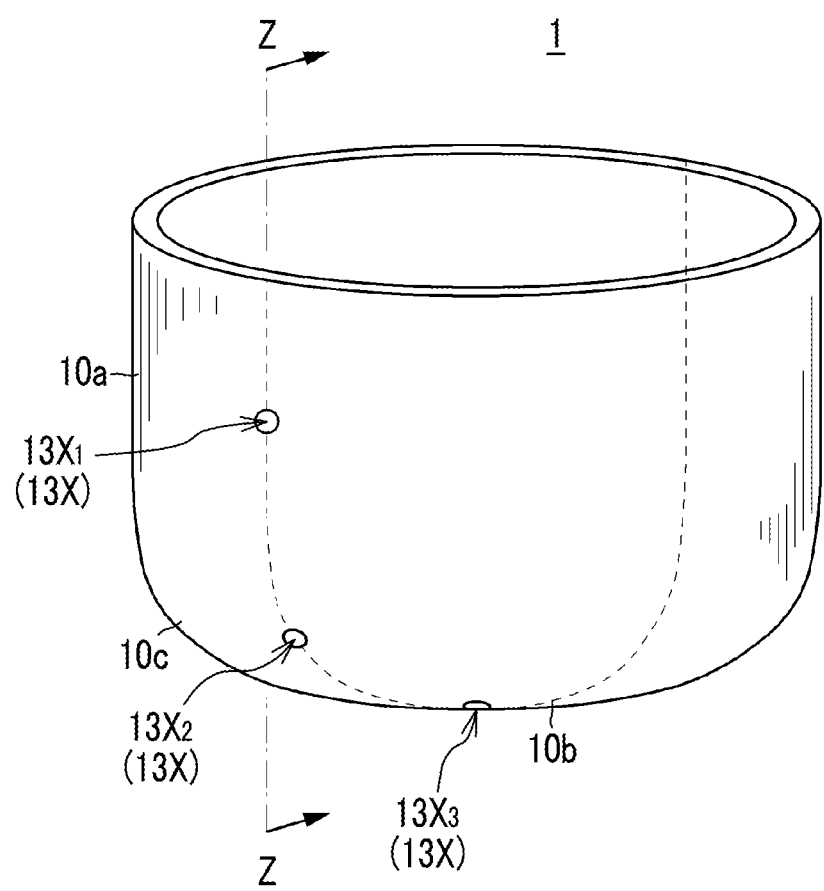
FIG. 8 is a schematic perspective view illustrating the configuration of a quartz glass crucible according to another embodiment of the present invention.

FIG. 8 is a schematic perspective view illustrating the configuration of a quartz glass crucible according to another embodiment of the present invention. In addition, FIG. 9 is a schematic side cross-sectional view of the quartz glass crucible of FIG. 8.

Figure 9:
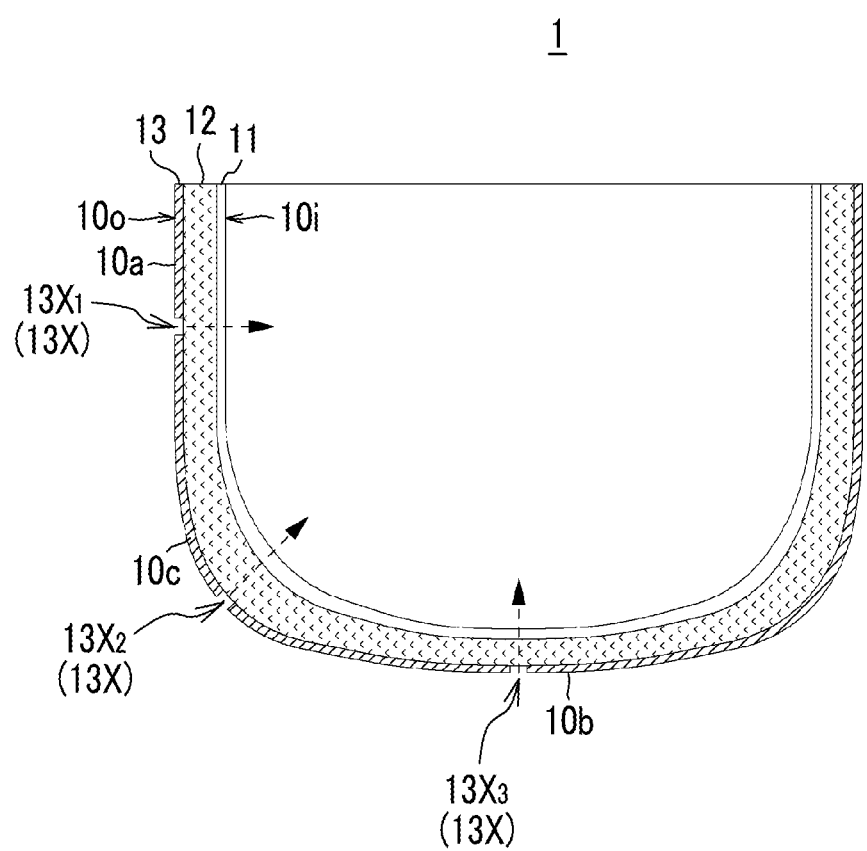
FIG. 9 is a schematic side cross-sectional view of the quartz glass crucible of FIG. 8.

As illustrated in FIG. 8 and FIG. 9, the feature of the quartz glass crucible 1 is that a semi-molten layer removed portion 13X from which a portion of the semi-molten layer 13 is removed is included while maintaining a state where the quartz glass crucible 1 can be used in a step of pulling up a silicon single crystal. The semi-molten layer removed portion 13X is a region from which a portion of the semi-molten layer 13 has been removed. However, a portion of the semi-molten layer 13 is not necessary to be completely removed as described above, and it is sufficient that the crucible is processed so that the surface roughness of the outer surface of the crucible on which the semi-molten layer 13 is formed becomes low to some extent. Since the semi-molten layer-removed portion 13X is a region in which the semi-molten layer is partially removed, the semi-molten layer-removed portion 13X is surrounded by the semi-molten layer 13.

The quartz glass crucible 1 of the present embodiment has the side wall portion 10a, the bottom portion 10b, and the corner portion 10c, and has a first semi-molten layer-removed portion $13X_1$ provided in the side wall portion 10a, a second semi-molten layer-removed portion $13X_2$ provided in the corner portion, and a third semi-molten layer-removed portion $13X_3$ provided in the bottom portion. In each part of the crucible, only one semi-molten layer-removed portion 13X may be provided, or a plurality of semi-molten layer-removed portions 13X may be provided. For example, one semi-molten layer-removed portion 13X may be provided on the upper side and one lower side of the side wall portion 10a, or three or more semi-molten layer-removed portions 13X may be provided at regular intervals. In this case, it is preferable that the plurality of semi-molten layer-removed portions 13X provided at each portion of the crucible are provided on a scanning line connecting the center of the bottom portion of the crucible and an arbitrary point at the upper end of the rim as shown in the drawing.

The size of the semi-molten layer-removed portion 13X is not particularly limited as long as infrared transmissivity can be measured, but is preferably set to be as small as possible so as not to adversely affect the properties of the quartz glass crucible. As described above, by providing the plurality of semi-molten layer-removed portions 13X on the outer surface 10o of the quartz glass crucible 1, infrared transmissivity of the quartz glass crucible that is not affected by the semi-molten layer can be inspected substantially nondestructively. Therefore, a silicon single crystal can be pulled up using the quartz glass crucible 1 after the inspection.

While the preferred embodiments of the present invention have been described above, the present invention is not limited to the embodiments and may be variously modified without departing from the scope of the present invention. Accordingly, all such modifications are naturally included in the scope of the present invention.

For example, in the above embodiments, destructive inspection was performed in which infrared transmissivity was measured using a crucible piece cut out from the quartz glass crucible, or the semi-molten layer of a portion of the outer surface of the crucible was removed in which infrared transmissivity was measured by irradiating the exposed portion with infrared light in a nondestructive manner without destroying the quartz glass crucible. In a case where this nondestructive inspection is performed, it is possible to provide a quartz glass crucible after measuring infrared transmissivity for the manufacturing of a silicon single crystal by the Czochralski method.

Example 1

<Discussion on Relationship Between Surface Roughness of Semi-Molten Layer and Infrared Transmissivity>

The effect of the semi-molten layer on infrared transmissivity of the crucible was discussed. In this discussion, first, a quartz glass crucible having an aperture of 800 mm (32 inches) was prepared, a crucible piece of about 30 mm square was cut out from the side wall portion thereof, and without polishing the semi-molten layer of the outer surface of the crucible piece sample, the surface roughness of the outer surface was measured according to the standard of JIS B 0601-2001. The arithmetic average roughness Ra was 30 μm.

Next, infrared transmissivity of the crucible piece sample was measured. In the measurement of infrared transmissivity, a laser power meter (light-receiving device) with a light-receiving portion diameter of 22 mm was installed at a position 43 mm from an infrared lamp having a wavelength of 0.5 to 3.5 μm and a peak wavelength of 1.0 μm, and the crucible piece sample of about 30 mm square was placed on the light-receiving portion. When a value of the transmitted light measured was referred to as W1 and a value in a blank state in which the sample was not placed on the light-receiving portion was referred to as W0, infrared transmissivity was set to W1/W0×100 [%]. As a result, infrared transmissivity of the crucible piece sample was 36%.

Next, after slightly polishing the outer surface of the crucible piece sample, the outer surface roughness of the outer surface was measured, and the arithmetic average roughness Ra was 20 μm. When infrared transmissivity of the crucible piece sample was measured, the infrared transmissivity was 38%.

Next, after further polishing the outer surface of the crucible piece sample, the surface roughness of the outer surface was measured, and the arithmetic average roughness Ra was 15 μm. When infrared transmissivity of the crucible piece sample was measured, the infrared transmissivity was 49%.

Next, after further slightly polishing the outer surface of the crucible piece sample, the surface roughness of the outer surface was measured, and the arithmetic average roughness Ra was 5 μm. When infrared transmissivity of the crucible piece sample was measured, the infrared transmissivity was 49%, which was the same as the previous measurement.

From the above results, it was found that when the outer surface of the quartz glass crucible is polished and smoothed until the arithmetic average roughness Ra of the outer surface reaches 15 μm, infrared transmissivity of the crucible can be evaluated with substantially no effect of the semi-molten layer.

<Discussion on Infrared Transmissivity of Each Part of Crucible Measured by Removing Semi-Molten Layer>

Samples #1 to #12 of quartz glass crucibles having an aperture of 800 mm (32 inches) were prepared, and after removing the semi-molten layer, the arithmetic surface roughness Ra of the outer surface of the crucibles was measured. Ra was about 1 to 2 μm. Subsequently, infrared transmissivity of each part of the crucibles was measured. The measurement position of the side wall portion of the crucibles was set to the center position of the side wall portion of the crucibles in the height direction, the measurement position of the corner portion was set to the maximum thickness position of the corner portion, and the measurement position of the bottom portion was set to the center position of the bottom portion of the crucibles. The measurement method of infrared transmissivity is as described above. Thereafter, using crucibles #1 to #12 manufactured under the same conditions as the crucibles used for the measurement of infrared transmissivity, silicon single crystals were grown by the CZ method under the same pulling-up conditions.

Next, a wafer sample was sampled from the silicon single crystals and the oxygen concentration thereof was measured. Specifically, the sampling position was set so that the solidification rate was within a range of 30 to 60%, five wafer samples were acquired from the same position within this range, the oxygen concentration (Old ASTM_F121 (1979)) was measured, and the average oxygen concentration value was calculated. FIG. 10 shows the measurement results of the oxygen concentration of the single crystal pulled up from the crucible samples #1 to #12.

Infrared transmissivities of the side wall portion, the corner portion, and the bottom portion of Sample #1 of the quartz glass crucible according to Example 1 were 55%, 46%, and 52%, respectively. The oxygen concentration in the silicon single crystal pulled up using this crucible Sample #1 was a particularly low value in the range of $9 \times 10^{17}$ to $12 \times 10^{17}$ atoms/cm$^3$, and no dislocation had occurred in the single crystal.

Infrared transmissivities of the side wall portion, the corner portion, and the bottom portion of Sample #2 of the quartz glass crucible according to Example 2 were 70%, 25%, and 50%, respectively. The oxygen concentration in the silicon single crystal pulled up using this crucible Sample #2 was a particularly low value in the range of $9 \times 10^{17}$ to $12 \times 10^{17}$ atoms/cm$^3$, and no dislocation had occurred in the single crystal.

Infrared transmissivities of the side wall portion, the corner portion, and the bottom portion of Sample #3 of the quartz glass crucible according to Example 3 were 56%, 33%, and 36%, respectively. The oxygen concentration in the silicon single crystal pulled up using this crucible Sample #3 was a particularly low value in the range of $9 \times 10^{17}$ to $12 \times 10^{17}$ atoms/cm$^3$, and no dislocation had occurred in the single crystal.

Infrared transmissivities of the side wall portion, the corner portion, and the bottom portion of Sample #4 of the quartz glass crucible according to Example 4 were 84%, 46%, and 57%, respectively. The oxygen concentration in the silicon single crystal pulled up using this crucible Sample #4 was a particularly low value in the range of $9 \times 10^{17}$ to $12 \times 10^{17}$ atoms/cm$^3$, and no dislocation had occurred in the single crystal.

Infrared transmissivities of the side wall portion, the corner portion, and the bottom portion of Sample #5 of the quartz glass crucible according to Example 5 were 52%, 51%, and 70%, respectively. The oxygen concentration in the silicon single crystal pulled up using this crucible Sample #5 was a value in the range of $9 \times 10^{17}$ to $12 \times 10^{17}$ atoms/cm$^3$, and no dislocation had occurred in the single crystal.

Infrared transmissivities of the side wall portion, the corner portion, and the bottom portion of Sample #6 of the quartz glass crucible according to Example 6 were 46%, 39%, and 51%, respectively. The oxygen concentration in the silicon single crystal pulled up using this crucible Sample #6 was a value in the range of $9 \times 10^{17}$ to $12 \times 10^{17}$ atoms/cm$^3$, and no dislocation had occurred in the single crystal.

Infrared transmissivities of the side wall portion, the corner portion, and the bottom portion of Sample #7 of the quartz glass crucible according to Comparative Example 1 were 86%, 65%, and 59%, respectively, and the infrared transmissivity of the corner portion was high. The oxygen concentration in the silicon single crystal pulled up using this crucible sample #7 was higher than $12 \times 10^{17}$ atoms/cm$^3$ and did not reach the target value of a low oxygen concentration. However, no dislocation had occurred in the single crystal.

Infrared transmissivities of the side wall portion, the corner portion, and the bottom portion of Sample #8 of the quartz glass crucible according to Comparative Example 2 were 52%, 58%, and 72%, respectively, and the infrared transmissivity of the corner portion was high. The oxygen concentration in the silicon single crystal pulled up using this crucible Sample #8 was higher than $12 \times 10^{17}$ atoms/cm$^3$ and did not reach the target value of a low oxygen concentration. However, no dislocation had occurred in the single crystal.

Infrared transmissivities of the side wall portion, the corner portion, and the bottom portion of Sample #9 of the quartz glass crucible according to Comparative Example 3 were 56%, 20%, and 33%, respectively, and the infrared transmissivities of the corner portion and the bottom portion were low. The oxygen concentration in the silicon single crystal pulled up using this crucible Sample #9 was a particularly low value in the range of $9 \times 10^{17}$ to $12 \times 10^{17}$ atoms/cm$^3$. However, dislocations had occurred in the single crystal.

Infrared transmissivities of the side wall portion, the corner portion, and the bottom portion of Sample #10 of the quartz glass crucible according to Comparative Example 4 were 39%, 24%, and 46%, respectively, and the infrared transmissivities of the side wall portion and the corner portion were low. The oxygen concentration in the silicon single crystal pulled up using this crucible Sample #10 was in the range of $9 \times 10^{17}$ to $12 \times 10^{17}$ atoms/cm$^3$. However, dislocations had occurred in the single crystal.

Infrared transmissivities of the side wall portion, the corner portion, and the bottom portion of Sample #11 of the quartz glass crucible according to Comparative Example 5 were 50%, 20%, and 40%, respectively, and the infrared transmissivity of the corner portion was low. The oxygen concentration in the silicon single crystal pulled up using this crucible Sample #11 was in the range of $9 \times 10^{17}$ to $12 \times 10^{17}$ atoms/cm$^3$. However, dislocations had occurred in the single crystal.

Infrared transmissivities of the side wall portion, the corner portion, and the bottom portion of Sample #12 of the quartz glass crucible according to Comparative Example 6 were 50%, 55%, and 40%, respectively, and the infrared transmissivity of the corner portion was high. The oxygen concentration in the silicon single crystal pulled up using this crucible Sample #12 was higher than $12 \times 10^{17}$ atoms/cm$^3$ and did not reach the target value of a low oxygen concentration. However, no dislocation had occurred in the single crystal.

<Discussion on Relationship Between Evaluation Method of Infrared Transmissivity and Oxygen Concentration in Silicon Single Crystal>

Six samples A1 to F1 of a 32-inch quartz glass crucible were prepared, and the infrared transmissivities of these samples were evaluated using the evaluation methods of the related art and the present invention. Specifically, first, the infrared transmissivity was measured as it was without scraping the outer surface of the final product of the quartz glass crucible. Thereafter, the infrared transmissivity was measured in a state where the outer surface was scraped to remove the semi-molten layer. The measurement position of the infrared transmissivity at this time was set to the maximum thickness position of the corner portion of the crucible, which has a high correlation with the crystal oxygen concentration. In addition, the measurement point of infrared transmissivity was set to four points (90-degree spacing) of the crucible in the circumferential direction, and the average value of infrared transmissivities at the four points was used as the final measured value. The measurement of infrared transmissivity of the crucible was a destructive inspection, in which a portion was cut out from the corner portion of the crucible, and infrared transmissivity before and after removing the semi-molten layer on the outer surface thereof was measured. FIG. 11 shows the measurement results of infrared transmissivity of the corner portion by the evaluation methods of the related art and the present invention.

Next, using Samples A2 to F2 for pulling up crystals of six quartz crucibles respectively manufactured under the same conditions as Samples A1 to F1 for infrared transmissivity evaluation, silicon single crystals were grown under the same conditions by the Czochralski method. As described above, the measurement of infrared transmissivity of the crucibles is a destructive inspection, and the exact same crucibles cannot be used. Therefore, crucible Samples A2 to F2 manufactured under the same conditions as Samples A1 to F1 were regarded as substantially the same crucibles, and silicon single crystals were pulled up.

Next, a wafer sample was sampled from the silicon single crystals pulled up using each of crucible Samples A2 to F2, and the oxygen concentration of each wafer was measured. Five wafer samples cut out from the same part where the solidification rate of the silicon single crystal was within a range of 30 to 60% were acquired, the oxygen concentration (Old ASTM_F121 (1979)) of each wafer was measured, and the average value of the oxygen concentration measured values was obtained. The results are shown in FIG. 11 together with the infrared transmissivities.

FIGS. 12 (a) and (b) are a scatter plot and a regression line showing the relationship between infrared transmissivity of the quartz glass crucible shown in FIG. 11 and the crystal oxygen concentration, in which FIG. 12 (a) particularly shows the evaluation method of the related art and FIG. 12 (b) particularly shows the evaluation method of the present invention. The horizontal axis of FIGS. 12 (a) and (b) represents the measured value (%) of the infrared transmissivity, and the vertical axis represents the crystal oxygen concentration ($\times 10^{17}$ atoms/cm$^3$).

As shown in FIG. 12 (a), the coefficient of determination $R^2$ of the regression line of the crystal oxygen concentration with respect to the infrared transmissivity of the crucible measured by the evaluation method of the related art became 0.623. On the other hand, as shown in FIG. 12 (b), the coefficient of determination $R^2$ of the regression line of the crystal oxygen concentration with respect to the infrared transmissivity measured by the evaluation method of the present invention became 0.9196, so that the correlation with the crystal oxygen concentration was higher than that of the evaluation method of the related art. From the above results, it was confirmed that the evaluation method of the present invention in which the infrared transmissivity is measured by removing the semi-molten layer is a suitable evaluation method of the infrared transmissivity of the quartz glass crucible.

REFERENCE SIGNS LIST

1 Quartz glass crucible
1s Crucible piece
5 Silicon melt
10a Side wall portion
10b Bottom portion
10c Corner portion
10i Inner surface of crucible
10o Outer surface of crucible
11 Transparent layer
12 Bubble layer
13 Semi-molten layer
16 Deposition layer of raw material silica powder
16A Synthetic silica powder
16B Natural silica powder
20 Carbon susceptor
21 Infrared lamp
22 Laser power meter
30 Mold
30i Inner surface of mold
31 Arc electrode
32 Vent hole

The invention claimed is:

1. A quartz glass crucible comprising:
a cylindrical side wall portion;
a bottom portion; and
a corner portion connecting the side wall portion and the bottom portion to each other;
wherein the cylindrical side wall portion, the bottom portion, and the corner portion are constituted by:
a transparent layer made of quartz glass that does not contain bubbles;
a bubble layer formed outside the transparent layer and made of quartz glass containing bubbles; and
a semi-molten layer formed outside the bubble layer and made of raw material silica powder solidified in a semi-molten state,
wherein the transparent layer and the bubble layer in the corner portion constitute a first laminate having a first infrared transmissivity which is 25 to 51% in a thickness direction,
the transparent layer and the bubble layer in the side wall portion constitute a second laminate having a second infrared transmissivity which is 46 to 84% in a thickness direction and which is higher than the first infrared transmissivity, and
the transparent layer and the bubble layer in the bottom portion constitute a third laminate having a third infrared transmissivity which is 36 to 70% in a thickness direction and which is higher than the first infrared transmissivity, and
wherein the bubble layer in the side wall portion has a thickness which is greater than a thickness of the transparent layer in the side wall portion, and
the bubble layer in the corner portion has a thickness which is greater than the thickness of transparent layer in the side wall portion.

2. The quartz glass crucible according to claim 1,
wherein the infrared transmissivity of the side wall portion in the state where the semi-molten layer is removed is higher than the infrared transmissivity of the bottom portion in the state where the semi-molten layer is removed.

3. The quartz glass crucible according to claim 2,
wherein the first laminate has a first thermal conductivity which is $1.5 \times 10^{-3}$ to $5.8 \times 10^{-3}$ cal/cm·s·° C.,
the second laminate has a second thermal conductivity which is higher than the first thermal conductivity, and
the third laminate has a third thermal conductivity which is higher than the first thermal conductivity.

4. The quartz glass crucible according to claim 2,
wherein a thickness of the bubble layer of the corner portion is 10 to 35 mm,
a thickness of the bubble layer of the side wall portion is 1 to 21 mm, and
a thickness of the bubble layer of the bottom portion is 4 to 21 mm.

5. The quartz glass crucible according to claim 1,
wherein the first laminate has a first thermal conductivity which is $1.5\times10^{-3}$ to $5.8\times10^{-3}$ cal/cm·s·° C.,
the second laminate has a second thermal conductivity which is higher than the first thermal conductivity, and
the third laminate has a third thermal conductivity which is higher than the first thermal conductivity.

6. The quartz glass crucible according to claim 5,
wherein the thermal conductivity of the side wall portion in the state where the semi-molten layer is removed is $3.5\times10^{-3}$ to $15.0\times10^{-3}$ cal/cm·s·° C., and
the thermal conductivity of the bottom portion in the state where the semi-molten layer is removed is $2.7\times10^{-3}$ to $13.2\times10^{-3}$ cal/cm·s·° C.

7. The quartz glass crucible according to claim 1,
wherein a thickness of the bubble layer of the corner portion is 10 to 35 mm,
a thickness of the bubble layer of the side wall portion is 1 to 21 mm, and
a thickness of the bubble layer of the bottom portion is 4 to 21 mm.

* * * * *